(12) United States Patent
Hendricksen et al.

(10) Patent No.: US 6,955,679 B1
(45) Date of Patent: Oct. 18, 2005

(54) EVERTER AND THREADTHROUGH SYSTEM FOR ATTACHING GRAFT VESSEL TO ANASTOMOSIS DEVICE

(75) Inventors: Michael Hendricksen, Menlo Park, CA (US); Theodore Bender, Palo Alto, CA (US); Brendan M. Donohoe, San Francisco, CA (US); Jaime Vargas, Palo Alto, CA (US); Andrew Frazier, Sunnyvale, CA (US); Stephen Yencho, Menlo Park, CA (US); Bernard Hausen, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 253 days.

(21) Appl. No.: 10/135,669

(22) Filed: Apr. 30, 2002

Related U.S. Application Data

(63) Continuation of application No. 09/440,116, filed on Nov. 15, 1999, now Pat. No. 6,402,764.

(51) Int. Cl.⁷ .............................................. A61B 17/04
(52) U.S. Cl. ..................................................... 606/149
(58) Field of Search ................................. 606/149, 153, 606/148; 623/1.14, 1.11, 1.13

(56) References Cited

U.S. PATENT DOCUMENTS

| | | | |
|---|---|---|---|
| 2,940,452 A | 6/1960 | Smialowski | |
| 3,057,355 A | 10/1962 | Smialowski et al. | |
| 3,180,337 A | 4/1965 | Smialowski | |
| 3,908,662 A | 9/1975 | Razgulov et al. | |
| 4,214,587 A | 7/1980 | Sakura, Jr. | |
| 4,352,358 A | 10/1982 | Angelchik | |
| 4,366,819 A | 1/1983 | Kaster | |
| 4,470,415 A | 9/1984 | Wozniak | |
| 4,553,542 A | 11/1985 | Schenck et al. | |
| 4,593,693 A | 6/1986 | Schenck | |
| 4,622,970 A | 11/1986 | Wozniak | |
| 4,624,255 A | 11/1986 | Schenck et al. | |
| 5,234,447 A | 8/1993 | Kaster et al. | |
| 5,336,233 A | 8/1994 | Chen | |
| 5,366,462 A | 11/1994 | Kaster et al. | |
| 5,676,670 A | 10/1997 | Kim | |
| 5,695,504 A | 12/1997 | Gifford, III et al. | |
| 5,707,362 A | 1/1998 | Yoon | |
| 5,817,113 A | 10/1998 | Gifford, III et al. | |
| 5,957,938 A | 9/1999 | Zhu et al. | 606/149 |
| 5,976,161 A | 11/1999 | Kirsch | |
| 6,475,222 B1 * | 11/2002 | Berg et al. | 606/108 |
| 6,485,496 B1 | 11/2002 | Suyker et al. | 606/153 |
| 6,547,799 B2 | 4/2003 | Hess et al. | 606/149 |

FOREIGN PATENT DOCUMENTS

| | | |
|---|---|---|
| CN | 0616611 | 3/1961 |
| WO | 99/62415 | 12/1999 |
| WO | 00/56226 | 9/2000 |
| WO | 01/70119 | 9/2001 |

* cited by examiner

Primary Examiner—Cary E. O'Connor
(74) Attorney, Agent, or Firm—Brian A. Schar

(57) ABSTRACT

An everter and threadthrough system useful for attaching a graft vessel to a anastomosis device which can be used to attach a graft vessel to a target vessel without the use of conventional sutures. The threadthrough system engages an end of the graft vessel and pulls the graft vessel through a deployment tool until a portion of the graft vessel extends beyond a distal end of the anastomosis device mounted on the deployment tool. The everter includes a spreading mechanism which expands the end of the graft vessel and folds the expanded end over the anastomosis device. In the case where the anastomosis device includes barbs, the everter can effect penetration of the graft vessel by the barbs. Once the graft vessel is everted over the anastomosis device, the deployment tool can be used to attach the graft vessel to a target vessel.

18 Claims, 21 Drawing Sheets

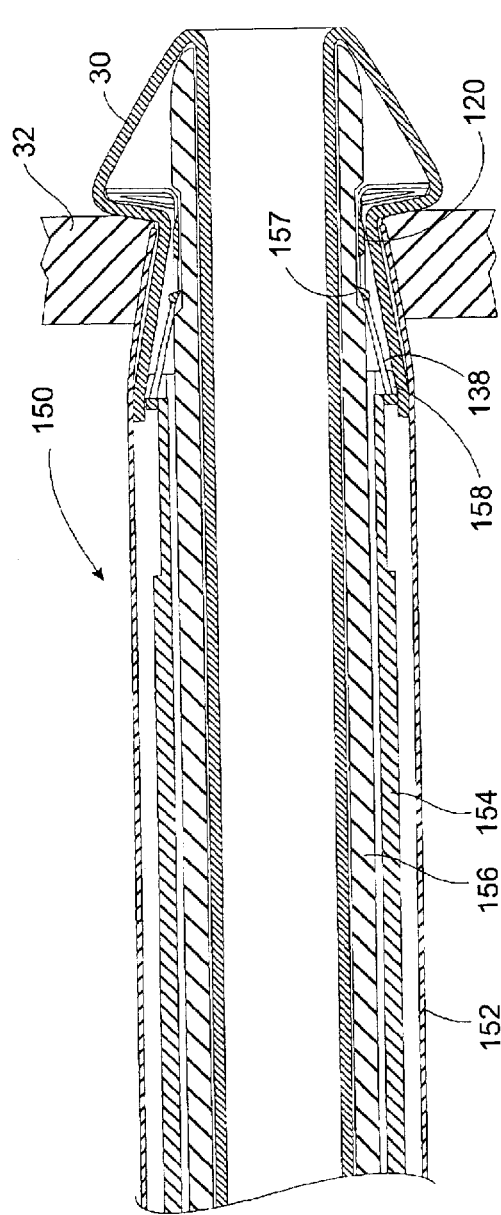
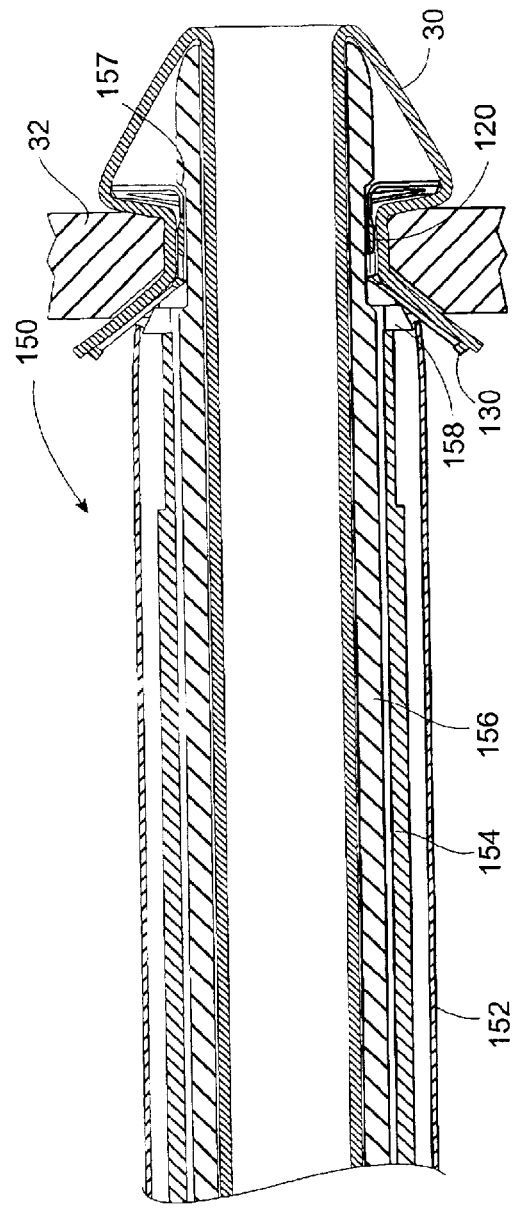
FIG. 7
FIG. 8

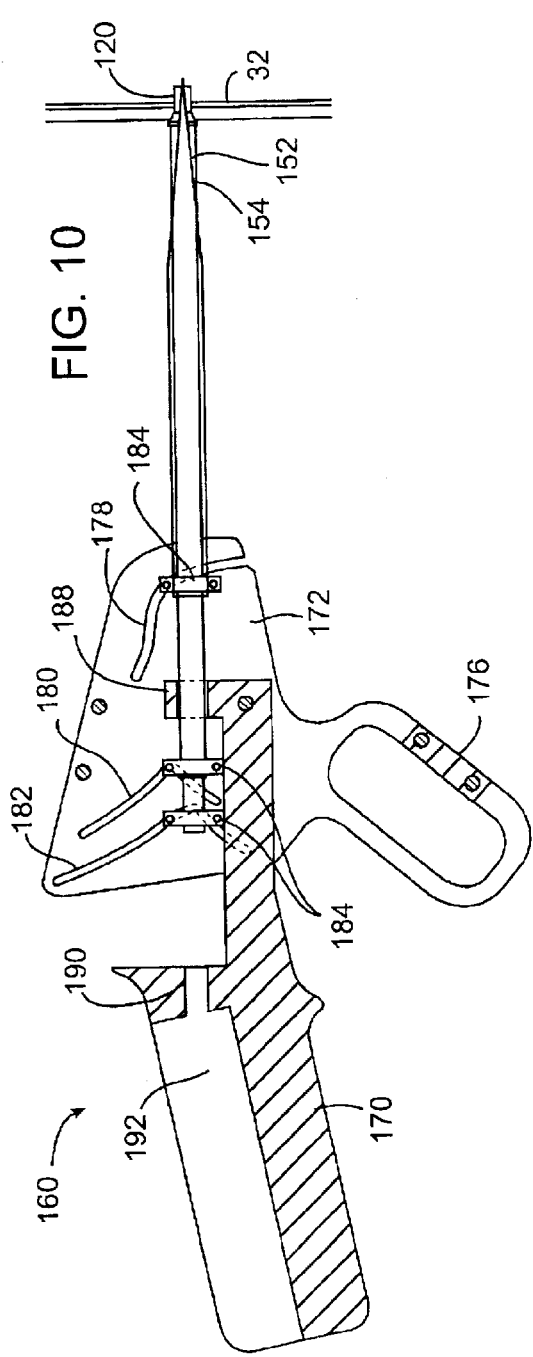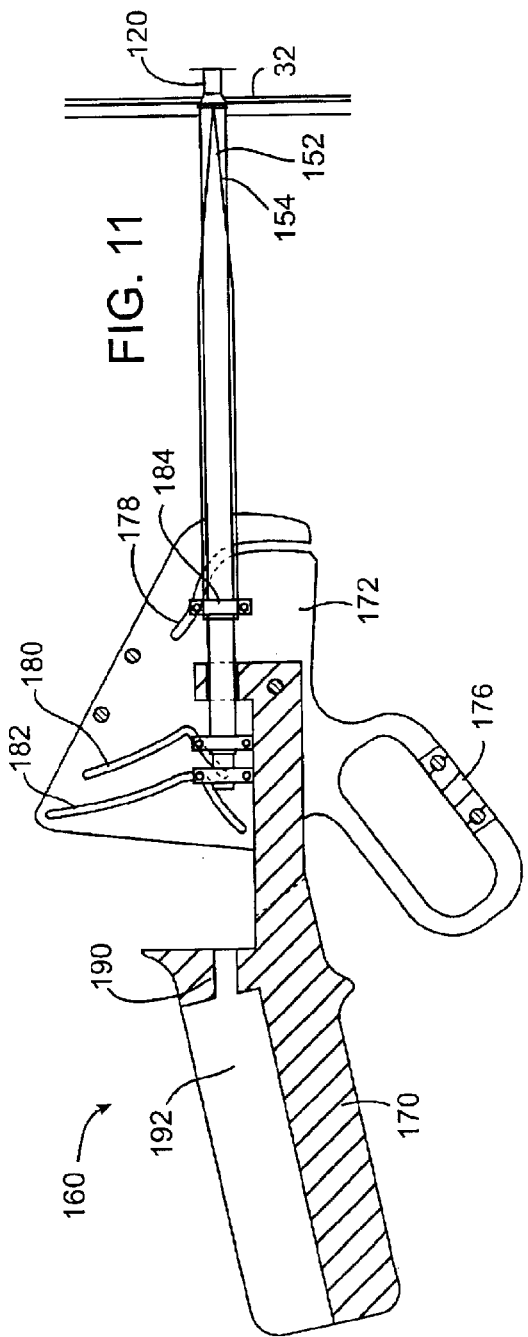

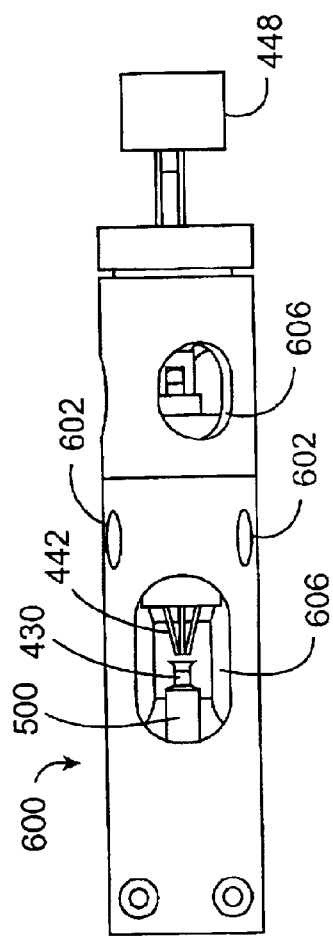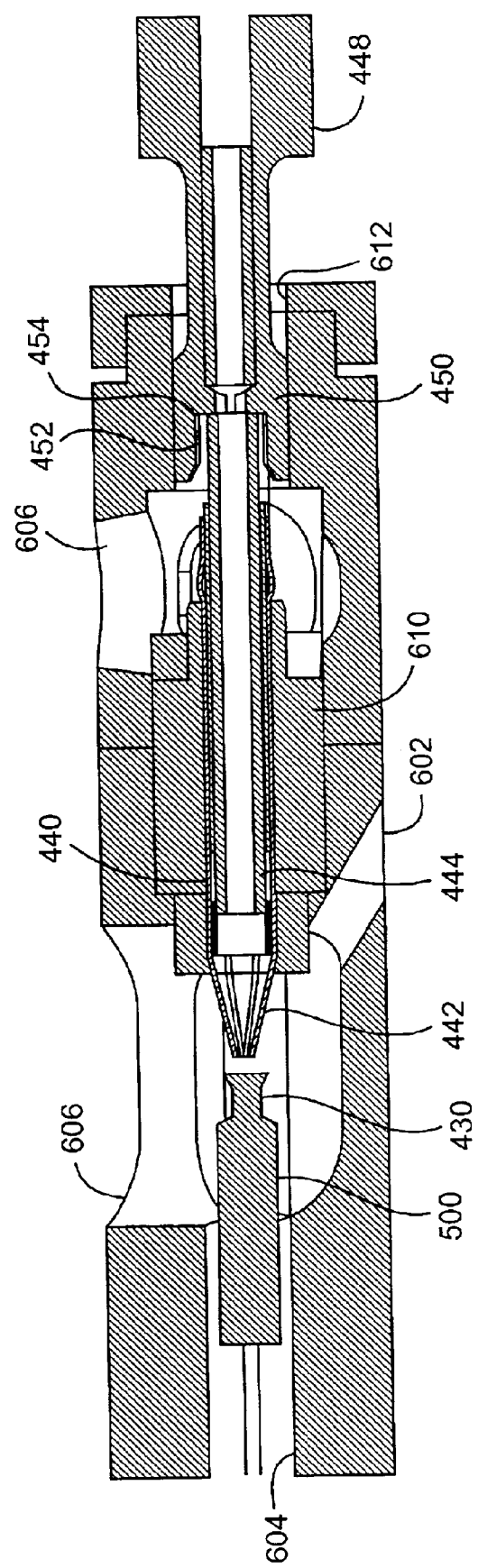
FIG. 30
FIG. 31

EVERTER AND THREADTHROUGH SYSTEM FOR ATTACHING GRAFT VESSEL TO ANASTOMOSIS DEVICE

This application is a continuation of U.S. patent application Ser. No. 09/440,116, now U.S. Pat. No. 6,402,764 filed on Nov. 15, 1999.

BACKGROUND OF THE INVENTION

1. Field of the Invention

The invention relates to an everter and threadthrough device for attaching a graft vessel to an anastomosis device which can be used for forming a sutureless connection between a bypass graft and a blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patients blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

An additional problem with CABG is the formation of thrombi and atherosclerotic lesions at and around the grafted artery, which can result in the reoccurrence of ischemia. The thrombi and atherosclerotic lesions may be caused by the configuration of the sutured anastomosis site. For example, an abrupt edge at the anastomosis site may cause more stenosis than a more gradual transition.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

The invention provides an everter tool useful for everting an end of a graft vessel over an end of an anastomosis device. The everter tool preferably includes a mechanism which expands an end of a graft vessel and everts the end of the graft vessel over an anastomosis device mounted on a deployment tool. For instance, the mechanism can include a first member having fingers at a distal end thereof, the fingers being expandable from a first configuration which fits within the end of the graft vessel to a second configuration which expands the end of the graft vessel, and an optional second member cooperating with the first member such that the second member is movable from a first location at which the fingers are in the first configuration to a second location at which the second member expands the fingers to the second configuration.

The everter tool can include various features. For example, the everter tool can be slidably received in a bore of an everter fixture and a handle on the everter tool can be used to engage a first portion of the handle with the first member and a second portion of the handle with the second member, the handle being movable in an axial direction such that the second portion pushes the second member along the first member until a distal end of the second member expands the fingers from the first configuration to the second configuration after which the first portion pushes the first member along the bore until the fingers evert the graft vessel. In such a case, a deployment tool having an anastomosis device mounted on a distal end thereof and a graft vessel fitted through the anastomosis device can be located in the bore of the housing such that the fingers can be pushed into a portion of the graft vessel extending beyond an end of the anastomosis device.

In order to locate the graft vessel in the anastomosis device, a threadthrough device can be used for pulling the graft vessel through the anastomosis device. The threadthrough device can include a clamp which attaches to an end of the graft vessel and an extension attached to the clamp, the threadthrough device being sized to pass through the anastomosis device. The threadthrough device can also include a tongue pivotally connected to the clamp, the clamp being movable towards and away from the tongue such that the graft vessel can be clamped between the clamp and the tongue. In a preferred embodiment, the threadthrough device includes three clamps and the extension composes a wire connected to each of the class.

According to a preferred embodiment, the anastomosis device includes barbs for penetrating the graft vessel and the everter tool includes a membrane engageable with the anastomosis device such that the barbs penetrate the graft vessel when the membrane is pressed against the anastomosis device.

The invention also provides a method of everting a graft vessel onto an anastomosis device, the method comprising locating a graft vessel in an anastomosis device mounted on a deployment tool such that a first portion of the graft vessel is within the deployment tool and a second portion of the graft vessel extends from an end of the deployment tool, expanding the second portion of the graft vessel, and everting the second portion of the graft vessel over the anastomosis device.

The method can be carried out in any suitable manner. For instance, the step of locating the graft vessel in the anastomosis device can be carried out by attaching an end of the graft vessel to a threadthrough device and passing the threadthrough device through the deployment tool. The step of expanding the second portion of the graft vessel can be carried out by inserting an everter tool into the second portion of the graft vessel. In such a case, the everter tool can optionally be pressed against the distal end of the deployment tool until barbs on a distal end of the anastomosis device penetrate the graft vessel. The step of expanding the second portion of the graft vessel can be carried out by inserting fingers of the everter tool into the second portion of the graft vessel and expanding the fingers within the second portion of the graft vessel. The step of everting the second portion of the graft vessel can be carried out by pressing the everter tool against the deployment tool. The step of expanding the second portion of the graft vessel can be carried out by locating the deployment tool in a bore of an everter fixture and sliding the everter tool from a first position to a second position along the bore. The step of everting the second portion of the graft vessel can be carried out by sliding the everter from the second position to a third position along the bore. The step of locating he graft vessel in the anastomosis device can be carried out by passing a threadthrough device through the deployment tool, the threadthrough device having a clamp attached to an end of the graft vessel and a wire extending from the clamp, the wire being pulled through an angled hole in the fixture while the graft vessel is pulled through the anastomosis device. In such a case, the clamp can be designed to spring open after passing out of the anastomosis device leaving a segment of the graft vessel extending beyond a distal end of the anastomosis device. According to a preferred embodiment, the step of everting the graft vessel can be carried out by pressing a first portion of the everter tool against an annular section of the graft vessel and moving a second portion of the everter tool in contact with an inner surface of the graft vessel until the inner surface is turned inside out over the anastomosis device.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 7 is a side cross sectional view of the anastomosis device deployment system with an expanded first annular flange;

FIG. 8 is a side cross sectional view of the anastomosis device deployment system expanding a second annular flange;

FIG. 10 is a schematic side cross-sectional view of the deployment tool of FIG. 9 shown during an anastomosis device insertion step;

FIG. 11 is a schematic side cross-sectional view of the deployment tool of FIG. 9 shown during an anastomosis device expansion step;

FIGS. 30 and 31 show details of the fixture shown in FIG. 29;

DETAILED DESCRIPTION OF THE PREFERRED EMBODIMENTS

Figure 1:
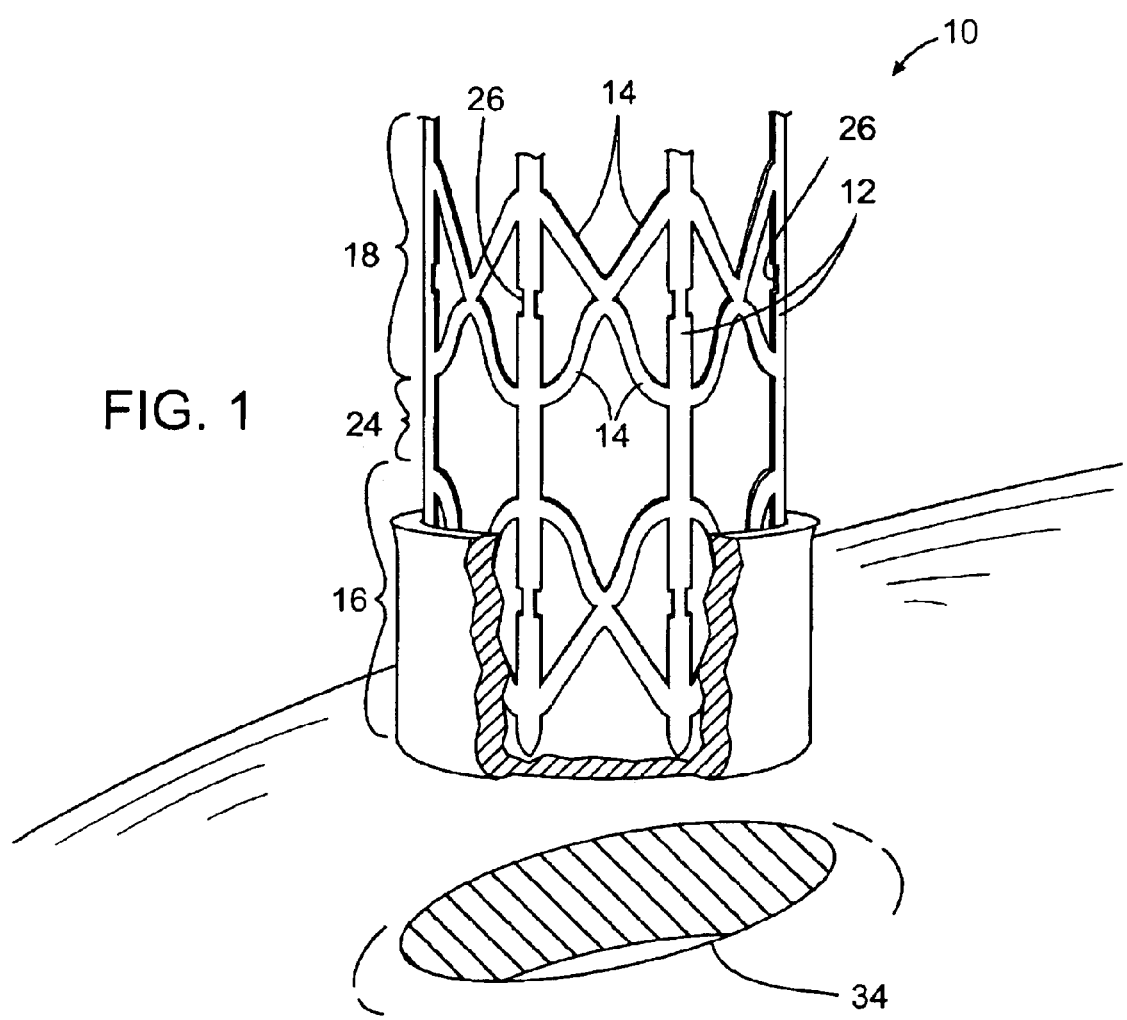
FIG. 1 is a perspective view of a first embodiment of an anastomosis device in a configuration prior to use with a graft vessel everted over the device.

According to the invention it is possible to perform a variety of anastomosis procedures, including coronary artery bypass grafting. The term "target vessel" is thus used to refer to vessels within the patient which are connected to either or both of the upstream and downstream end of the graft vessel. In such procedures, a large vessel anastomosis device is used with large diameter target vessels such as the aorta or its major side branches or a small vessel anatomic device is used for a target vessel which has a small diameter such as a coronary artery.

In deploying a large vessel anastomosis device, the device (with one end of a graft vessel attached thereto) is inserted into an incision in a wall of the target vessel with a deformable section in a first configuration, and the deformable section is radially expanded to a second configuration to deploy a flange. The flange applies an axial force against the wall of the target vessel. Additionally, the flange can be configured to apply a radial force, substantially transverse to the device longitudinal axis, against the wall of the target vessel, to secure the device to the target vessel. For example, the device can have a plurality of deformable sections forming distal and proximal flanges. With the proximal and distal end flanges deployed, the device can be prevented from shifting proximally out of the target vessel or distally further into the interior of the target vessel.

The large vessel devices can be configured to connect to target vessels of various sizes having a wall thickness of at least about 0.5 mm, and typically about 0.5 mm to about 5 mm. In a preferred embodiment of the invention, the large vessel anastomosis device is configured to longitudinally collapse as the deformable section is radially expanded. The surgeon can control the longitudinal collapse to thereby position the distal end flange at a desired location at least partially within the incision in the target vessel wall. The surgeon can also control the position of the proximal end flange by longitudinally collapsing the device to a greater or lesser degree, to thereby position the proximal end flange at a desired location in contact with the target vessel. Thus, regardless of the thickness of the target vessel wall, the device can be longitudinally collapsed to position the flanges against the target vessel wall and effectively connect the device thereto. This feature is significant because the device must be connected to target vessels which have a wide range of wall thickness. For example, the aortic wall thickness is typically about 1.4 mm to about 4.0 mm and the aorta diameter can range from about 25 to about 65 mm in diameter. Therefore, regardless of the thickness of the target vessel wall, the degree of deployment of the proximal end flange, and thus the longitudinal collapse of the device, can be controlled by the physician to thereby effectively connect the device to the target vessel. For example, the surgeon may choose between partially deploying the proximal end flange so that it is positioned against an outer surface of the target vessel wall, or fully deploying the flange to position it in contact with the media of the target vessel wall within the incision in the target vessel wall.

In deploying a small vessel anastomosis device, the device can be used on small target vessels having a wall thickness of less than about 1.0 mm, and typically about 0.1 mm to about 1 mm in the case of coronary arteries. Despite the small size of the target vessels, the small vessel devices provide sutureless connection without significantly occluding the small inner lumen of the target vessel or impeding the blood flow therethrough. For example, the small vessel devices can include an outer flange (with the graft vessel connected thereto) loosely connected to an inner flange before insertion into the patient with the space between the loosely connected inner and outer flanges being at least as great as the wall thickness of the target vessel so that the inner flange can be inserted through an incision in the target vessel and into the target vessel lumen, with the outer flange outside the target vessel. With the outer and inner flanges in place on either side of a wall of the target vessel, tightening the flanges together compresses a surface of the graft vessel against the outer surface of the target vessel. This configuration forms a continuous channel between the graft vessel and the target vessel, without the need to suture the graft vessel to the target vessel wall and preferably without the use of hooks or barbs which puncture the target vessel.

In a coronary bypass operation in accordance with the invention, a large vessel device can be used to connect the proximal end of the graft vessel to the aorta, and a small vessel device can be used to connect the distal end of the graft vessel to an occluded coronary artery. However, in patients with an extreme arteriosclerotic lesion in the aorta, which may result in serious complications during surgical procedures on the aorta, the surgeon may wish to avoid this region and connect the proximal end of the graft vessel to any other adjacent less diseased vessel, such as the arteries leading to the arms or head. Further, the devices can be used with venous grafts, such as a harvested saphenous vein graft, arterial grafts, such as a dissected mammary artery, or a synthetic prosthesis, as required.

Connection of the large vessel device does not require the stoppage of blood flow in the target vessel. Moreover, the anastomotic devices can be connected to the target vessel without the use of cardiopulmonary bypass. In contrast, anastomosis techniques wherein the aorta is clamped to interrupt blood flow to the area of the aortic wall to which a vein is to be anastomosed may result in liberation of plaques and tissue fragments which can lead to organ dysfunction, such as strokes, renal failure, or intestinal ischemia. However, severely diseased aortas may not provide an area suitable for clamping due to significant calcification of the aortic wall. In the anastomosis technique according to the invention, the surgeon does not need significant room inside the patient to connect the anastomotic devices to the target vessel. For example, unlike sutured anatomies which require significant access to the aorta for the surgeon to suture the graft vessel thereto, the anastomotic devices allow the proximal end of the graft vessel to be connected to any part of the aorta. All parts of the aorta are accessible to the large vessel anastomosis devices, even when minimally invasive procedures are used. Consequently, the graft vessel may be connected to the descending aortas so that the graft vessel would not be threatened by damage during a conventional in sternotomy if a second operation is required at a later time.

According to the invention, a sutureless connection can be provided between a graft and a target vessel, while minimizing thrombosis or restenosis associated with the anastomosis. The anastomotic devices can be attached to the target vessel inside a patient remotely from outside the patient using specially designed applicators, so that the devices are particularly suitable for use in minimally invasive surgical procedures where access to the anastomosis site is limited. The devices allow the anastomosis to be performed very rapidly, with high reproducibility and reliability, without clamping, and with or without the use of cardiopulmonary bypass.

According to one preferred method of deploying the anastomosis device, the surgeon operates a deployment tool using both hands. One hand supports the tool via a handle while the other twists an actuation knob to deploy the anastomotic device. Locating the actuation knob on the tool's main axis minimizes the tendency of reaction forces to wobble the tool keeping it stable and in proper position during deployment. The twisting motion is converted to in displacements by a set of rotating cams that engage a trocar, holder, and expander. The cams control the sequence of relative motions between the instrument's trocar and device deployment mechanisms.

During the foregoing procedure, a surgeon will place the tip of the instrument (the mechanical stop) in light contact with the site on the aorta to be anastomosed. Having located a suitable site, the surgeon then twists the actuation knob to fire the spring-loaded trocar and continues twisting to deploy the anastomotic device. The trocar penetrates the aortic wall at a high rate of speed to minimize any unintended deformation of the aorta and maintains a substantially fluid-tight seal at the puncture site. Having entered the aortic lumen, the trocar dilates as the anastomotic device and its holder tube (crown) are advanced through it, thus retracting the aortic tissue and serving as an introducer for the device. Once the device has filly entered the aortic lumen the trocar is withdrawn. The anastomotic device is then expanded to its full diameter and an inner flange is deployed. The device is then drawn outwards towards the instrument (mechanical stop) to seat the inner flange firmly against the intimal wall of the aorta. An outer flange is then deployed from the external side, compressing the aortic wall between the inner and outer flanges and the device is disengaged from the instrument completing the anastomosis.

Figure 2:
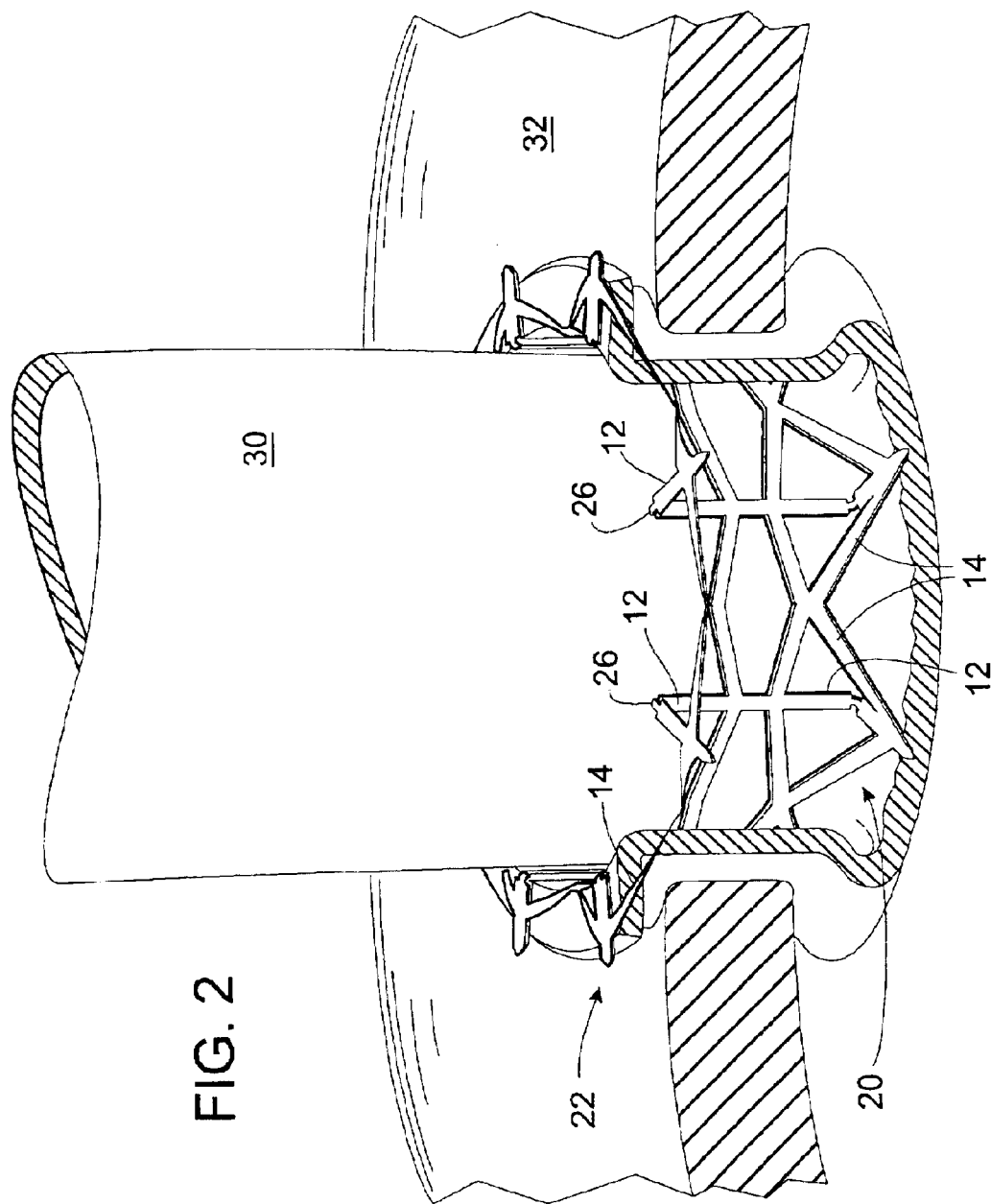
FIG. 2 is a perspective view of the anastomosis device of FIG. 1 in a deployed configuration.

FIG. 1 illustrates the distal portion of an anastomosis device 10 according to a first embodiment of the present invention, the proximal portion (not shown) being adapted to be deployed by a deployment tool which will be explained later. The anastomosis device 10 includes a plurality of axial members 12 and a plurality of struts 14 interconnecting the axial members. The axial members 12 and struts 14 form a first linkage 16 at a first end of the device and a second linkage 18 at a second end of the device. The first and second linkages 16, 18 form inner and outer flanges 20, 22 when the anastomosis device 10 is deployed as illustrated in FIG. 2. The deployed flanges 20, 22 may be annular ring shaped or conical in shape. The first and second linkages 16, 18 are connected by a central connecting portion 24.

In use, a graft vessel 30 is inserted through a center of the tubular anastomosis device 10 and is everted over the first linkage 16 at the first end of the device. The first end of the device may puncture part way or all the way through the graft vessel wall to hold the graft vessel 30 on the device. An opening 34 is formed in the target vessel 32 to receive the graft vessel 30 and anastomosis device 10. Once the anastomosis device 10 with everted graft vessel 30 are inserted through the opening 34 in the target vessel 32, the inner and outer flanges 20, 22 are formed as shown in FIG. 2 to secure the graft vessel to the target vessel by trapping the wall of the target vessel between the two flanges. The anastomosis device 10 forms a smooth transition between the target vessel 32 and the graft vessel 30 which helps to prevent thrombi formation.

The inner and outer flanges 20, 22 are formed by radial expansion of the anastomosis device 10 as follows. The first and second linkages 16, 18 are each made up of a plurality of axial members 12 and struts 14. The struts 14 are arranged in a plurality of diamond shapes with adjacent diamond shapes connected to each other to form a continuous ring of diamond shapes around the device. One axial member 12 extends through a center of each of the diamond shapes formed by the struts 14. A reduced thickness section 26 or hinge in each of the axial members 12 provides a location for concentration of bending of the axial members. When an expansion member of a deployment tool such as a rod or balloon is inserted into the tubular anasmosis device 10 and used to radially expand the device, each of the diamond shaped linkages of struts. 14 are elongated in a circumferential direction causing a top and bottom of each of the diamond shapes to move closer together. As the top and bottom of the diamond shapes move closer together, the axial members 12 bend along the reduced thickness sections 26 folding the ends of the device outward to form the inner and outer flanges 20, 22 with the result that the wall of the target vessel 32 is trapped between the flanges and the everted graft vessel 30 is secured to the target vessel.

In the anastomosis device 10 shown in FIGS. 1 and 2, the struts 14 may be straight or curved members having constant or varying thicknesses. In addition, the axial members 12 may have the reduced thickness sections 26 positioned at a center of each of the diamond shapes or off center inside the diamond shapes. The positioning and size of the reduced thickness sections 26 will determine the location of the flanges 20, 22 and an angle the flanges make with an a is of the device when fully deployed. A final angle between the flanges 20, 22 and longitudinal axis of the device 10 is about 40-140 degrees, preferably about 50–90 degrees.

Figure 3:
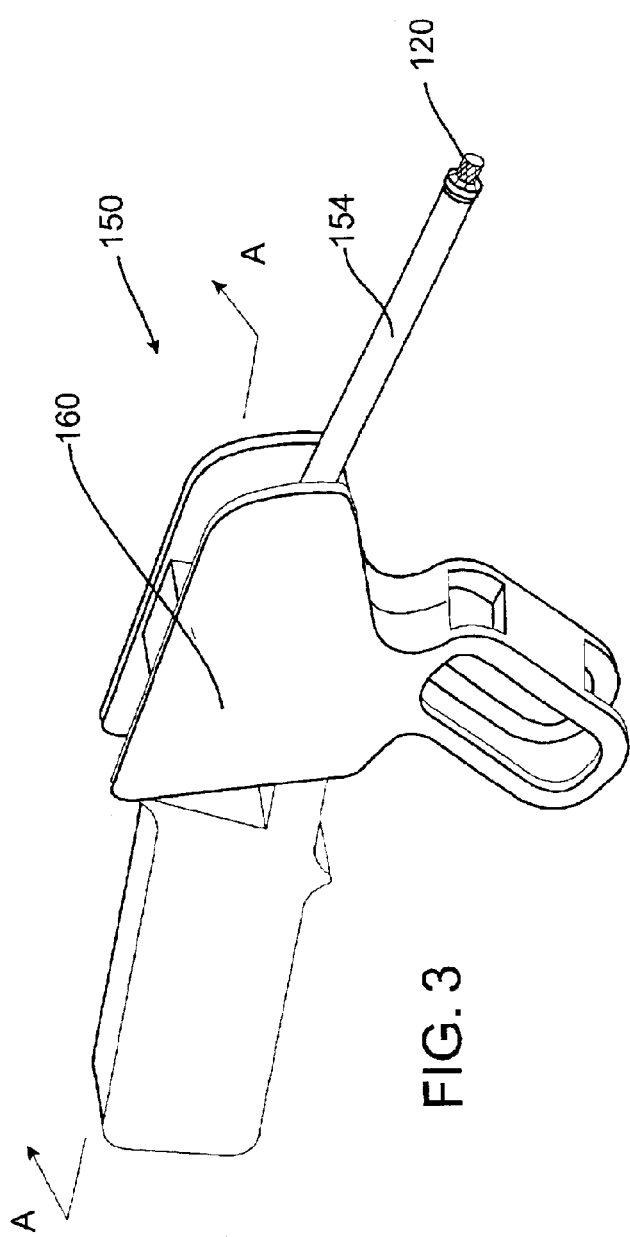
FIG. 3 is a perspective view of an anastomosis device deployment system.
Figure 4:
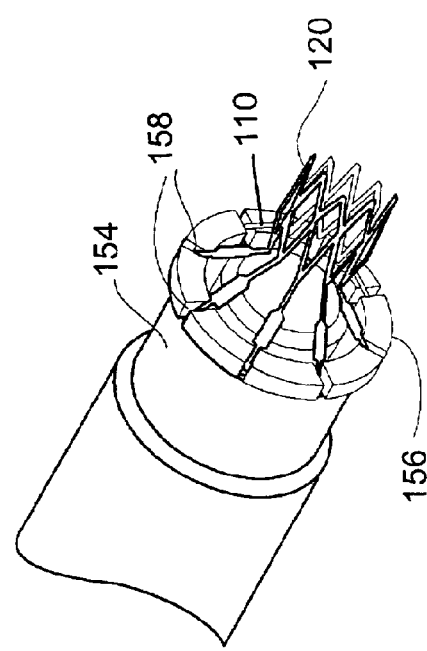
FIG. 4 is an enlarged perspective view of the distal end of the anastomosis device deployment system of FIG. 3 with an anastomosis device prior to deployment.
Figures 5, 6:
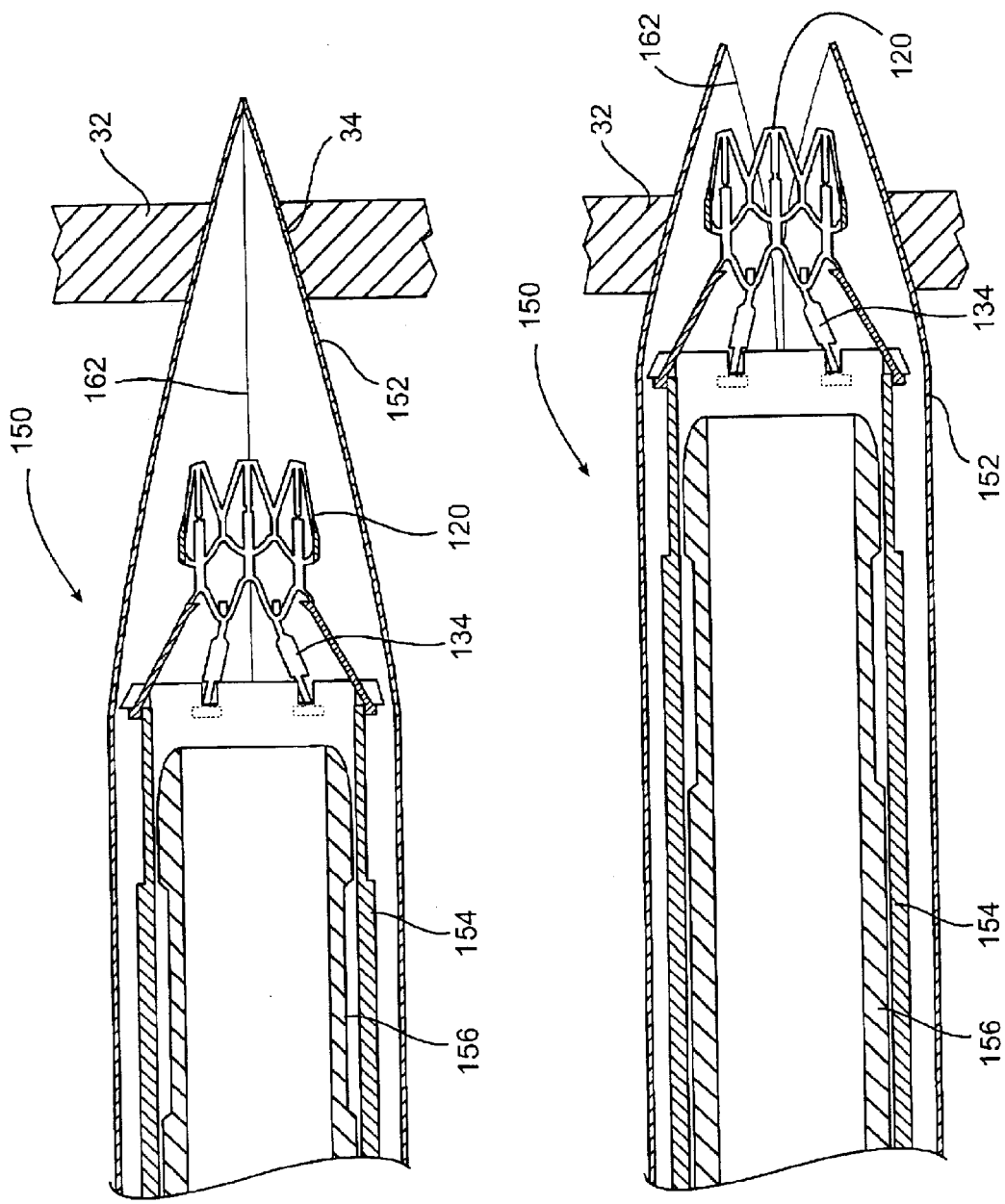
FIG. 5 is a side cross sectional view of the anastomosis device deployment system puncturing the target vessel to advance the anastomosis device into the target vessel wall.
FIG. 6 is a side cross sectional view of the anastomosis device deployment system advancing the anastomosis device into the target vessel wall.

FIGS. 3–7 illustrate a deployment system 150 and sequence of deploying an anastomosis device 120 such as the device shown in FIGS. 1–2 with the deployment system. In FIGS. 3–5 the graft vessel 30 has been eliminated for purposes of clarity. As shown in FIGS. 3–7, the deployment system 150 includes a hollow outer trocar 152 (not shown in FIG. 3), a holder tube 154 positioned inside the trocar, and an expander tube 156 slidable inside the holder tube. As can be seen in the detail of FIG. 4, the anastomosis device 120 is attached to a distal end of the holder tube 154 by inserting T-shaped ends 112 of pull tabs 110 in slots 158 around the circumference of the holder tube. The trocar 152, holder tube 154, and expander tube 156 are all slidable with respect to one another during operation of the device. A device handle 160 is provided for moving the tubes with respect to one another will be described in further detail below with respect to FIGS. 8–11.

As shown in FIG. 5, initially, the holder tube 154, expander tube 156, and the anastomosis device 120 are positioned within the tocar 152 for insertion The trocar 152 has a hollow generally conical tip with a plurality of axial slots 162 which allow the conical tip to be spread apart so that the anastomosis device 120 can slide through the opened trocar. The trocar 152, acting as a tissue retractor and guide, is inserted through the wall of the target vessel 32 forming an opening 34. As shown in FIG. 6, the anastomosis device 120 is then advanced into or through the target vessel wall 32 with the holder tube 154. The advancing of the holder tube 154 causes the distal end of the trocar 152 to be forced to spread apart. Once the anastomosis device 120 is in position and the trocar 152 has been withdrawn, the inner annular flange 20 is deployed by advancing the expander tube 156 into the anastomosis device. The advancing of the expander tube 156 increases the diameter of the anastomosis device 120 causing the inner flange to fold outward from the device. This expanding of the inner flange may be performed inside the vessel and then the device 120 may be drawn back until the inner flange abuts an interior of the target vessel wall 32.

As shown in FIG. 8, after the inner flange has been deployed, the holder tube 154 is advanced forming the outer flange. As the holder tube 154 is advanced, the anastomosis device 120 drops into a radial groove 157 on an exterior of the expander tube 156 which holds the anastomosis device stationary on the expander tube 156. The holder tube 154 is then moved forward to detach the entire anastomosis device by disengaging the pull tabs 130 from the slots 158 in the holder tube and causing the outer flange to be deployed. During deployment of the outer flange, shoulders 134 on the device, shown most clearly in FIGS. 5 and 6, engage a tapered distal end of the holder tube 154 causing the pull tabs 130 to be released from the slots 158. Alternatively, and as will be explained in connection with a frangible anastomosis device according to the invention, movement of the holder tube 154 can detach a deployed portion of the device from a throw away portion of the device which remains attached to the holder tube.

One alternative embodiment of the holder tube 154 employs a plurality of flexible fingers which receive the pull tabs 130 of the anastomosis device 120. According to this embodiment each pull tab 130 is received by an independent finger of the holder tube 154. To deploy the second or outer flange of the anastomosis device 120, the flexible fingers flex outward bending the pull tabs 130 outward.

FIGS. 9–12 illustrate the operation of the handle 160 to move the trocar 152, the holder tube 154, and the expander tube 156 with respect to one another to deploy the anastomosis device 120 according to the present invention. The handle 160 includes a grip 170 and a trigger 172 pivotally mounted to the grip at a pivot 174. The trigger 172 includes a finger loop 176 and three contoured cam slots 178, 180, 182 corresponding to the trocar 152, holder tube 154, and expander tube 156, respectively. Each of these tubes has a fitting 184 at a distal end thereof. A pin 186 connected to each of the fittings 184 slides in a corresponding one of the cam slots 178, 180, 182. A fourth cam slot and tube may be added to control deployment of the outer flange. Alternatively, the handle can be modified to include fewer cam slots for deployment of the inner and outer flanges.

The handle 160 is shown in FIG. 8 in an insertion position in which the trocar 152 extends beyond the holder tube 154 and the expander tube 156 for puncturing of the target vessel wall 32. Optionally, a flexible seal (not shown) such as heat shrinkable plastic tubing or a molded elastomer tubing can be provided on the outer surface of the trocar 152 such that the seal covers the axial slots 162 at a location spaced from the tip of the trocar to minimize leaking of blood from the target vessel after the incision is formed. In a preferred embodiment, the trocar is actuated by a mechanism which causes the trocar to penetrate the aorta wall at a high rate of speed to minimize deformation of the aorta and maintain a fluid tight seal at the puncture site in a manner similar to biopsy gun. For instance, the spring mechanism attached to the trocar and/or the handle can be used to fire the trocar at the incision site. Any suitable acting mechanism can be used to fire the trocar in accordance with the invention. As the trigger 172 is rotated from the position illustrated in FIG. 9 to the successive positions in FIGS. 10–12, the pins 186 slide in the cam slots 178, 180, 182 to move the trocar 152, holder tube 154 and expander tube 156.

Figure 9:
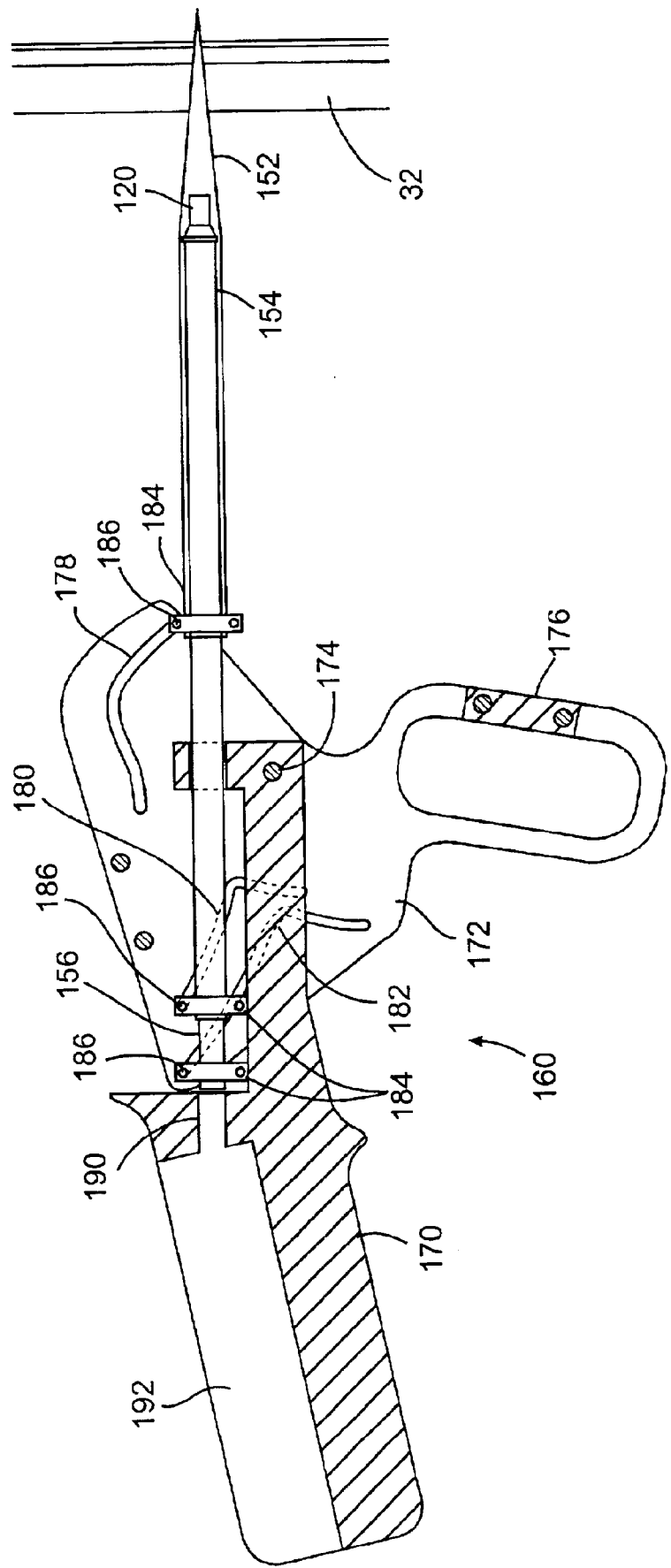
FIG. 9 is a schematic side cross-sectional view of a deployment tool taken along line A—A of FIG. 3, the deployment tool is shown during a vessel puncturing step.

FIG. 10 shows the handle 160 with the trigger 172 rotated approximately degrees from the position of FIG. 9. This rotation moves the holder tube 154 and expander tube 156 forward into the wall of the target vessel 32 spreading the trocar 152. The anastomosis device 120 is now in position for deployment. FIG. 11 shows the trigger 172 rotated approximately 45 degrees with respect to the position of FIG. 9 and the cam slot 182 has caused the expander tube 156 to be advanced within the holder tube 154 to deploy the inner flange. The trocar 152 has also been withdrawn.

Figure 12:
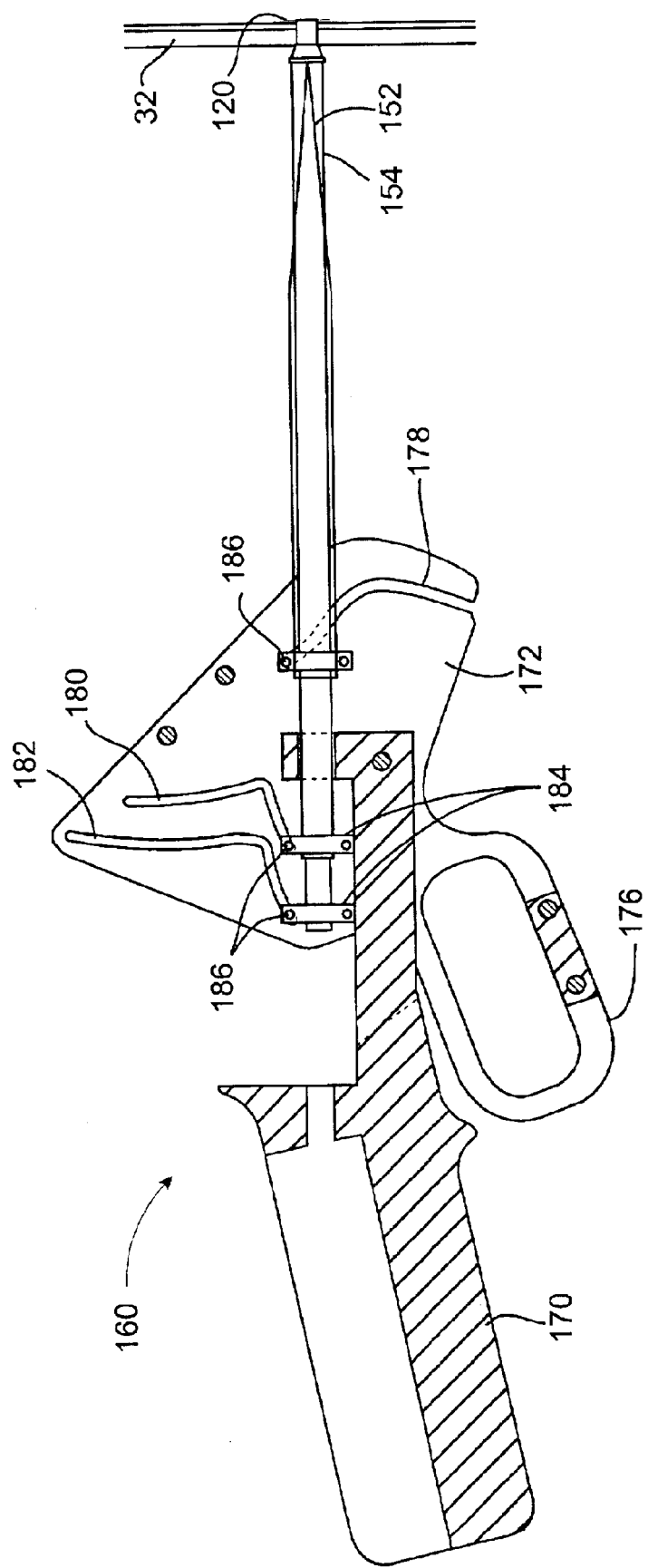
FIG. 12 is a schematic side cross-sectional view of the deployment tool of FIG. 9 shown after the anastomosis device has been fully deployed.

FIG. 12 shows the handle 160 with the trigger 172 pivoted approximately 60 degrees with respect to the position shown in FIG. 9. As shown in FIG. 12, the expander tube 156 has been withdrawn to pull the inner flange against the vessel wall 32 and the holder tube 154 is moved forward to deploy the outer flange and disengage the holder tube 154 from the anastomosis device 120.

The handle 160 also includes a first channel 188 and a second channel 190 in the grip 170 through which the graft vessel (not shown) may be guided. The grip 170 also includes a cavity 192 for protecting an end of the graft vessel opposite from the attachment end.

According to a preferred embodiment of the invention, the graft vessel can be everted over the anastomosis device in the following manner. First, the graft vessel is passed through the anastomosis device while the anastomosis device is mounted on the deployment tool. In this "threadthrough" process, a vein graft can be positioned inside the tool such that it is ready for eversion (described below). The vein graft begins this process at the back end of the tool. The threadthrough tool uses several sets of jaws to grab an end of the vein graft and draw it through the internal bore of the tool. The threadthrough process ends when the vein graft has been drawn through the tool and extends approximately ⅛ beyond the implant device.

In the next step, the graft vessel is folded over the anastomosis device. In this "eversion" process the vein graft is rolled back around the implant device such that the inner surface of the vein graft is facing away from the implant device. Eversion is achieved with an everter tool which fits within an eversion fixture, the everter tool including a set of everter fingers and a drum assembly comprised of an inner drum, an outer drum, and a drum membrane. The lumen of the vein graft is placed on the cone-shaped everter fingers which then expand the vein graft to a larger diameter. The drum assembly then pins the vein graft against the implant device while the everter fingers translate forward. This forward translation causes the vein graft to roll back onto the outside of the vein graft, exposing the vein graft's inner surface. This process is now explained with reference to FIGS. 13–31.

Figure 13:
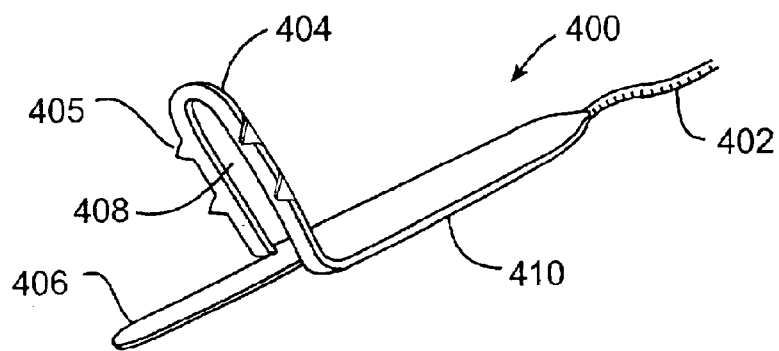
FIG. 13 shows details of a threadthrough device which can be used in a preferred technique for everting a graft vessel over an anastomosis device in accordance with the invention.
Figure 14:
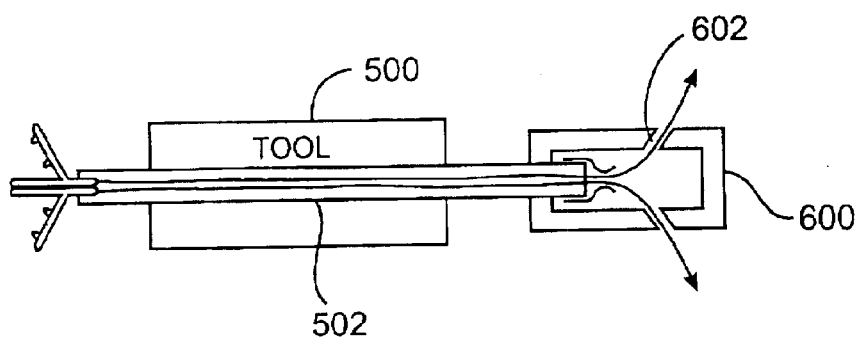
FIG. 14 shows how the theadthrough device of FIG. 13 can be passed through a deployment tool mounted in an everter fixture.

With reference to FIGS. 13–14, in a first step, a wire or wires 402 of a threadthrough device 400 are passed through a bore 502 of a deployment tool 500 having an anastomosis device mounted on the distal end thereof. The threadthrough tool 400 can include a plurality (e.g., two or three) threadthrough jaws 404, each of which is attached to the wire 402. As an example, the jaws 404 can be laser cut from stainless steel tubing in a manner which provides an opening 408 in each jaw 44 and a tongue 406 which lies in a plane contain main body. 410 of the jaw 404. The jaw 404 can be bent at an angle ranging from 30 to 90° to the tongue 406. In preparation for the thread through process, it is advantageous for the threadthrough tool 400 to be positioned inside the tool 500. The wire or wires 402 attached to the threadthrough jaws 404 can be inserted into the back end of the tool 500, threaded through the internal bore 502 of the tool 500, and passed out through the center of the implant device mounted on the end of the deployment tool.

As shown in FIG. 14, an eversion fixture 600 can be temporarily attached to the front end of the tool 500. The eversion fire can include exit channels 602 for the threadthrough wires 402, as well as assisting the eversion process described later. Each of the threadthrough wires 402 can exit the eversion fixture 600 through one or more angled exit channels 602. The wires 402 can be pulled to draw the threadthrough jaws 404 up to the back edge of the tool 500.

Figure 15:
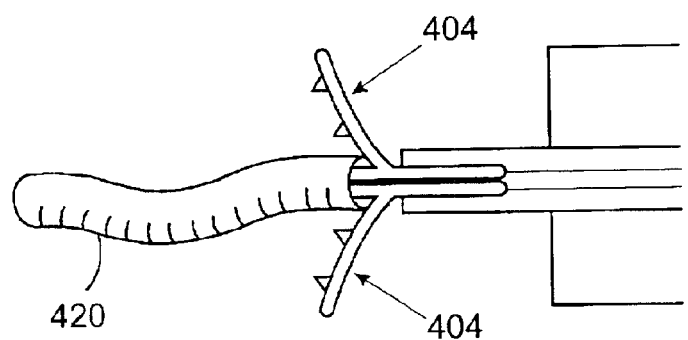
FIG. 15 shows how an end of a graft vessel can be prepared to be clamped by the threadthrough device.
Figure 16:
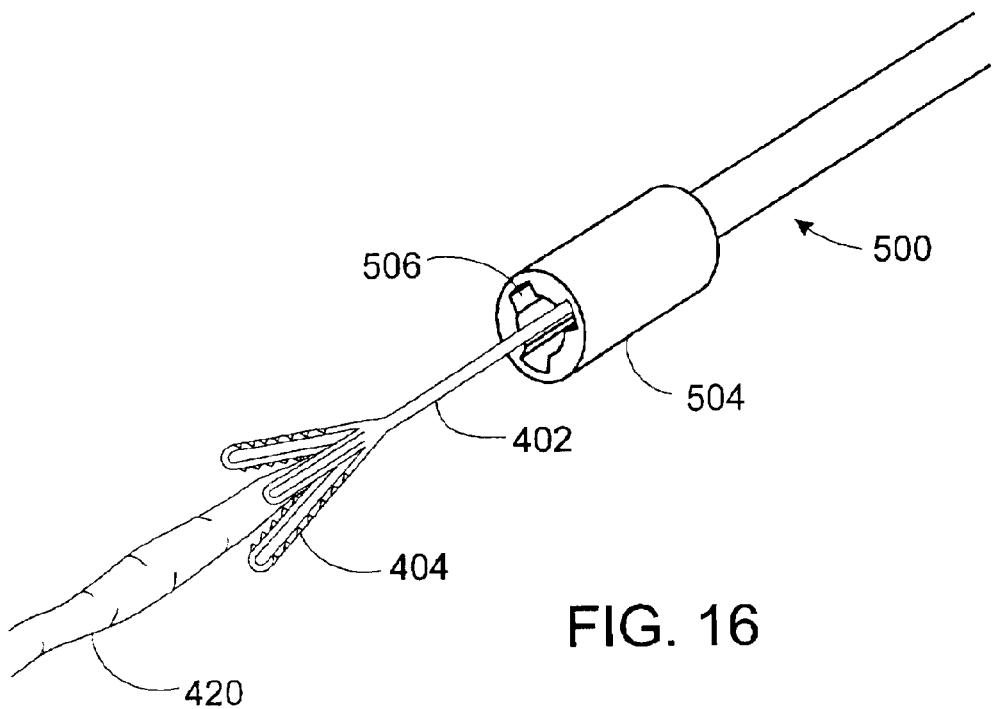
FIG. 16 shows how the threadthrough device can be passed through a funnel at the back end of a deployment tool.

In the next step, a vein graft 420 is placed over the tongues 406 and inside the jaws 404, as shown in FIG. 15. The vein graft 420 can be placed on the threadthrough tool 400 by using forceps to pull an end of the vein graft 420 over the tongues 406 which are clustered together providing a single extension to position inside the lumen of the vein graft 420. As shown in FIG. 16, a funnel 504 having tapered channels 506 at the back end of the tool 500 can be used to align the jaws 404 at equal increments apart from each other.

Figure 17:
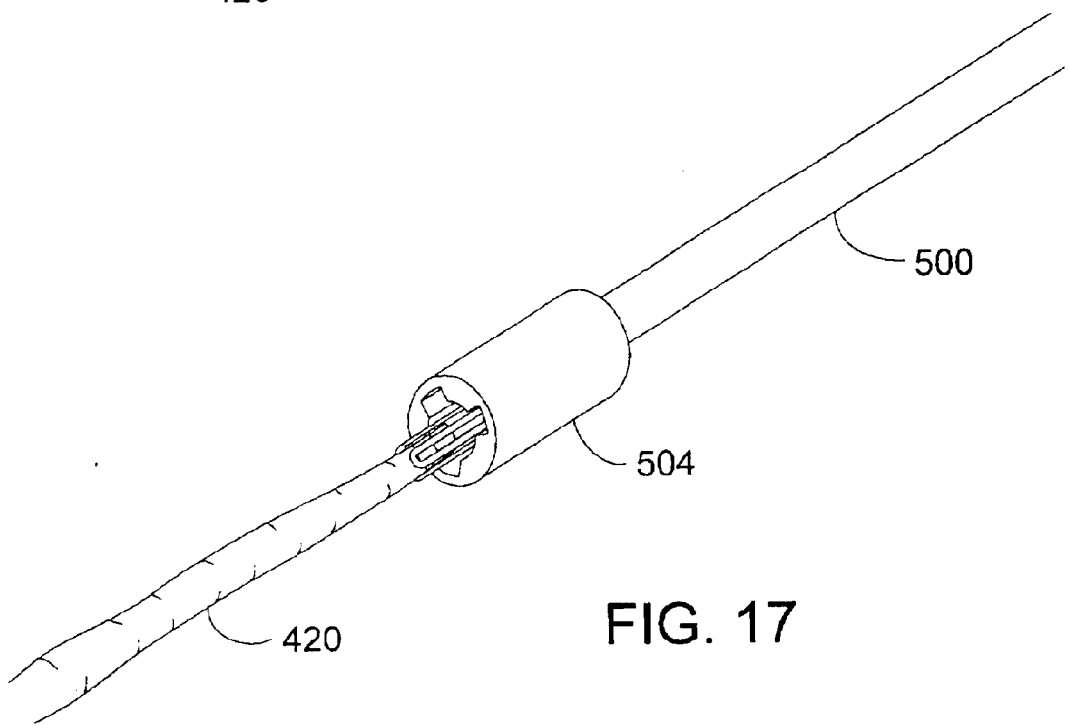
FIG. 17 shows how tapered grooves in the funnel align and close the jaws of the threadthrough device.

In the next step, the threadthrough wires 402 are pulled to draw the jaws 404 into the bore 502 of the tool 500, causing the jaws 404 to close and grasp the vein graft 420, as shown in FIG. 17. By pulling the end of the threadthrough wires 402, the jaws 404 are drawn into the bore of the funnel 504. Inside this limited space, the jaws 404 are elastically or plastically deformed to close onto the wall of the vein graft 420. The vein graft wall is then captured between the upper jaw 404 and its corresponding tongue 406. Teeth 405 along the surface of the jaws 404 facing the vein graft 420 provide additional friction to prevent the vein graft 420 from slipping out of the closed jaws 404.

Figure 18:
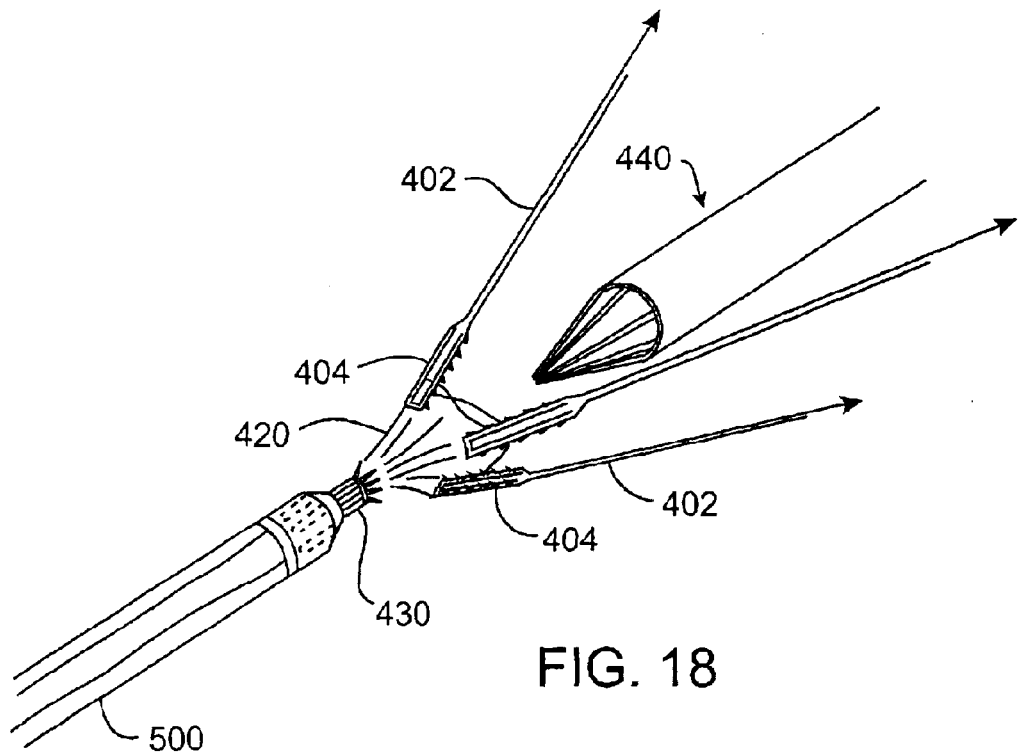
FIG. 18 shows how the jaws can be manipulated to introduce the lumen of the graft vessel to fingers of an everter tool after passing through the anastomosis device.

Next, the wires 402, jaws 404, and vein graft 420 are pulled through the tool 500 and the implant device 430, as shown in FIG. 18. The threadthrough wire or wires 402, the jaws 404 and vein graft 420 are drawn through the entire tool 500 and implant device until the jaws 404 begin to exit the implant device and draw a portion of the vein graft 420 out with them. The majority of the vein graft 420, however, remains inside the bore 502 of the tool 500. As explained below, an everter 440 is used to expand the end of the graft vein 420 and fold the expanded end over the outside of the device 430.

Figure 19:
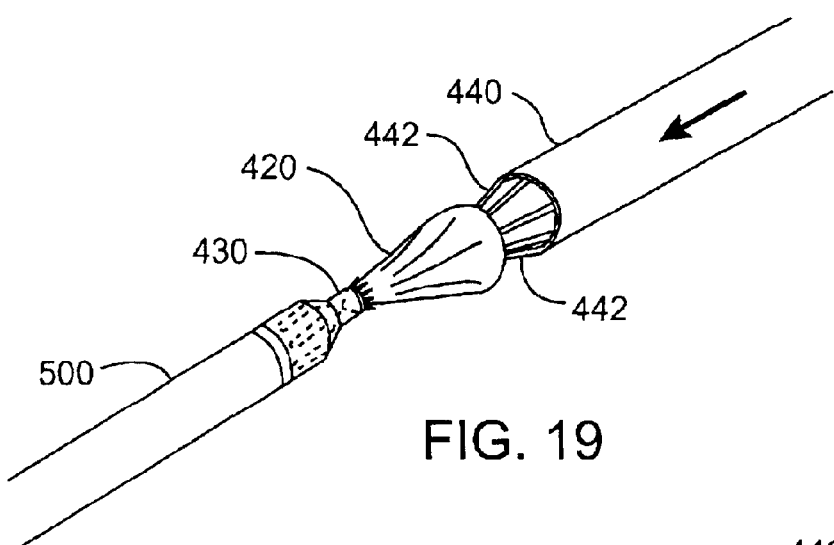
FIG. 19 shows how fingers of an everter tool can be inserted in the end of the graft vessel.
Figure 20:
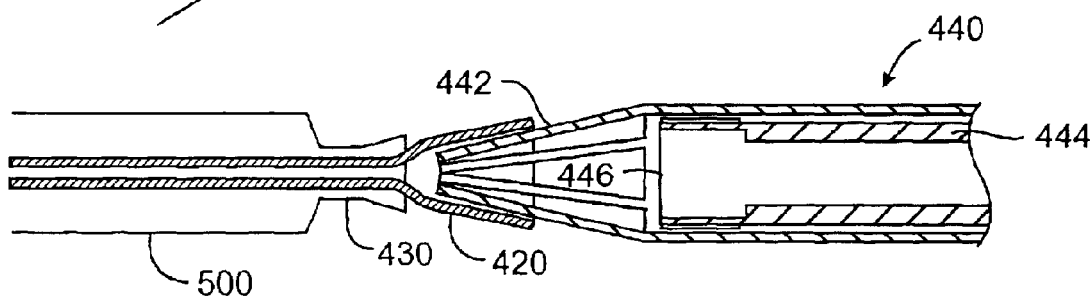
FIG. 20 shows details of the everter tool shown in FIG. 19.
Figure 21:
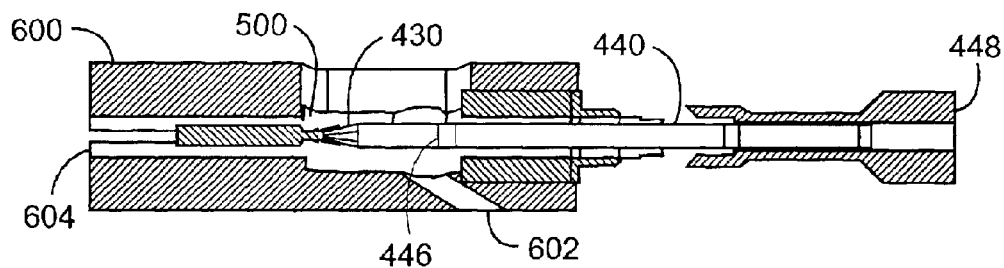
FIG. 21 shows details of an everter fixture.

In the following step, the vein graft 420 is positioned over a conical tip of the everter formed by a plurality of inwardly bent fingers 442 extending from the end of the everter 440, as shown in FIG. 19. As shown in FIG. 20, a drum assembly 444 having a membrane 446 at the end thereof is located within the everter 440. As shown in FIG. 21, the tool 500 and the everter 440 are located in a bore 604 of the everter fixture 600. The everter 440 and drum assembly 444 are moved along the bore 604 by a handle 448 attached to the everter/drum assembly. In operation, as the threadthrough wires 402 are drawn through their respective exit channels 602, the grasped section of the vein graft 420 is also forced toward the exit channels 602. This causes the vein graft 420 to open over the cone-shaped fingers 442 of the everter 440. Once the jaws 404 have emerged entirely from the implant device 430, they are then allowed to spring open, thereby releasing the vein graft 420. However, the jaws can be removed by cutting off the portion of the vein graft attached to the jaws or manually opening the jaws. After removal of the jaws from the vein graft, the vein graft 420 is left draped around the everter fingers 442 and the threadthrough wires 402 and jaws 404 are discarded.

Figure 22:
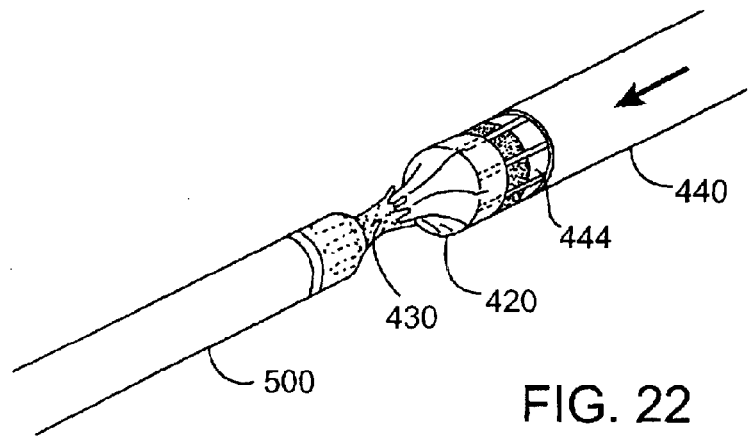
FIG. 22 shows details of how the graft vessel is expanded.

As shown in FIG. 22, the drum assembly 444 is pushed forward while the everter 440 and its fingers 442 remain stationary. As the drum assembly 444 advances, it expands the everter fingers 442 from the cone shape into more of a cylinder shape which expands the vein graft 420.

Figure 23:
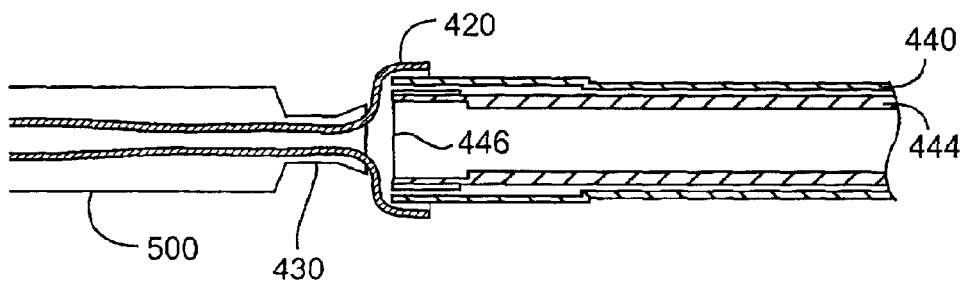
FIG. 23 shows details of the everter tool shown in FIG. 22.
Figure 24:
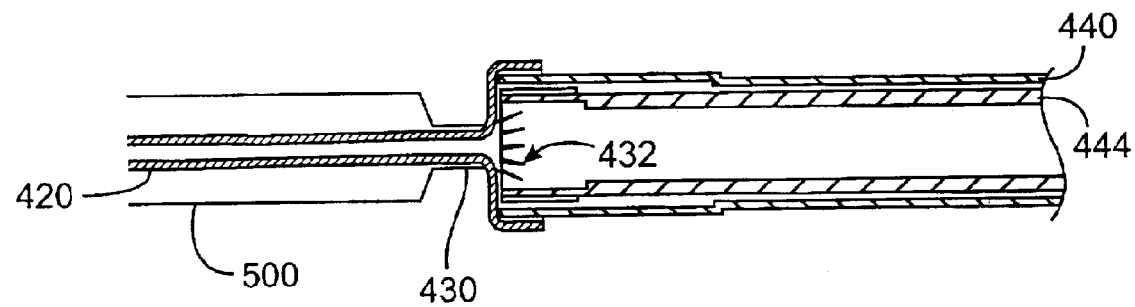
FIG. 24 shows details of how barbs on the anastomosis device penetrate through the graft vessel.
Figure 25:
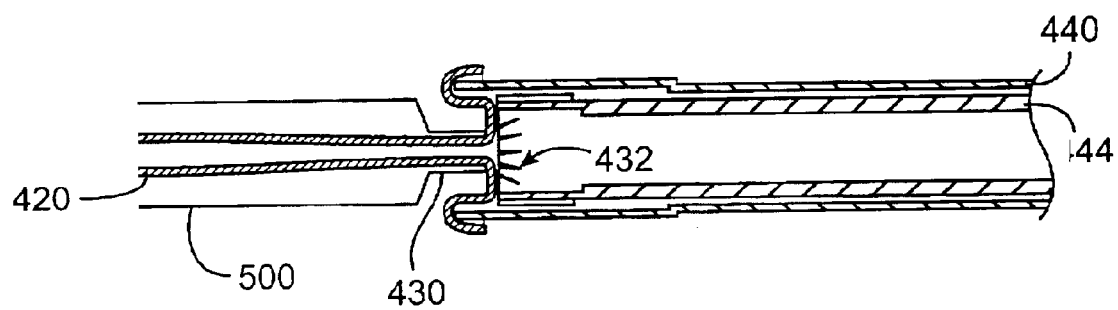
FIG. 25 shows details of the graft vessel is everted over the anastomosis device.
Figure 26:
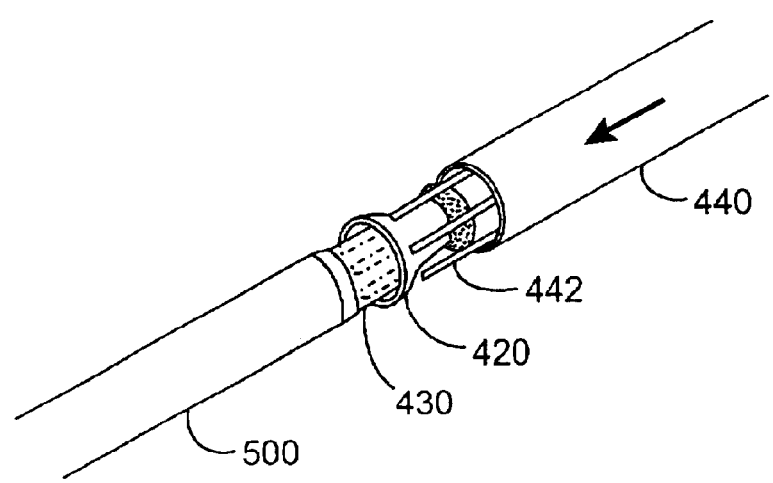
FIG. 26 shows the results of the eversion process.
Figure 27:
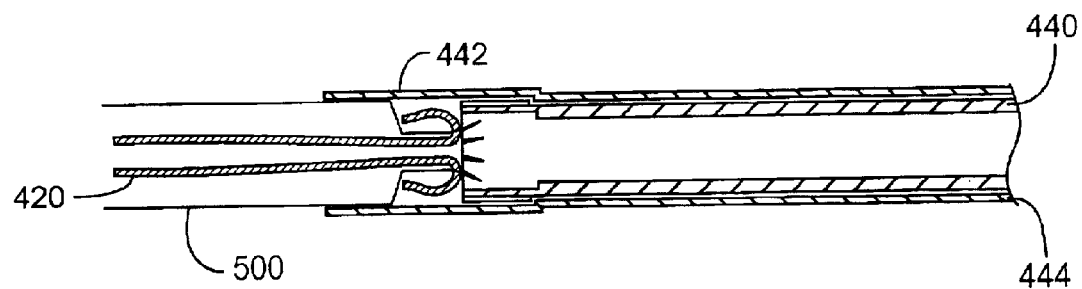
FIG. 27 shows details of the everter arrangement shown in FIG. 26.
Figure 28:
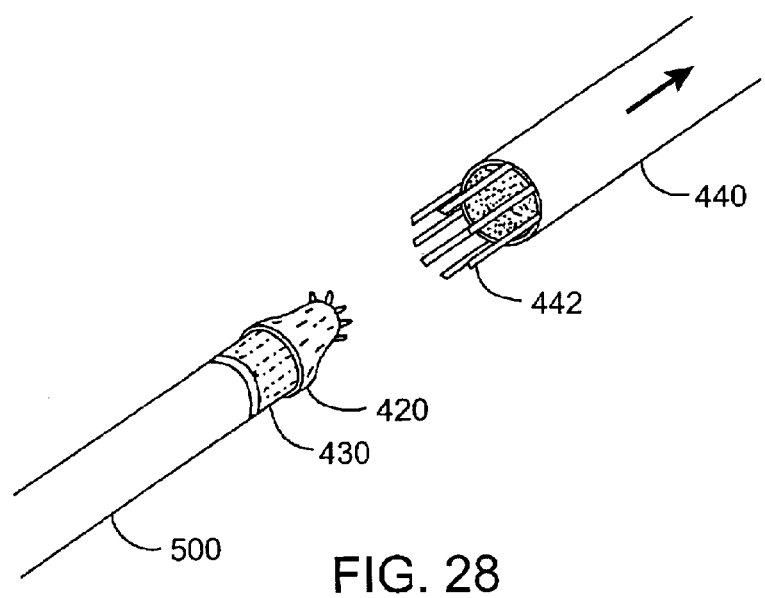
FIG. 28 shows the everter tool after separation from the deployment tool having the graft vessel everted over the anastomosis device.

Next, the drum assembly 444 and everter 440 are translated forward together at the same rate, as shown in FIG. 23. As they move forward together, the vein graft 420 is pushed forward into the implant device 430 by the drum membrane 446. The implant device preferably includes a plurality of axially extending barbs 432, as shown in FIG. 24, at the distal end thereof (e.g., eight circumferentially spaced apart sharpened tips). During advancement of the membrane 444, the membrane 446 presses against the axiauy eking tips of the implant device 430 causing the tips to penetrate the vein graft 420 and the drum membrane 446. This, in effect, pins the vein graft 420 in between the device 430 and the drum membrane 446 at the device tips. However, the penetration of the vein graft can be omitted or achieved in other ways as will be apparent to those skilled in the art In the next step, as shown in FIG. 25, the everter 440 is moved forward while maintaining the drum assembly 444 stationary. Because the vein graft is pinned at the implant device tips 432, the forward motion of the everter fingers 442 causes the vein graft 420 to roll around the tips of the everter fingers 442, pushing the vein graft 420 off of the everter 440 and onto the implant device 430. As shown in FIG. 26, further movement of the everter 440 causes the vein graft 420 to be pushed off of the everter 440 and onto the implant device 430. Eversion is finished once the vein graft 420 is completely off of the everter fingers 402 and only on the implant device 430, as shown in FIG. 27. After eversion is complete, the eversion hardware is removed, leaving only the evened vein graft 420 on the implant device 430.

Figure 29:
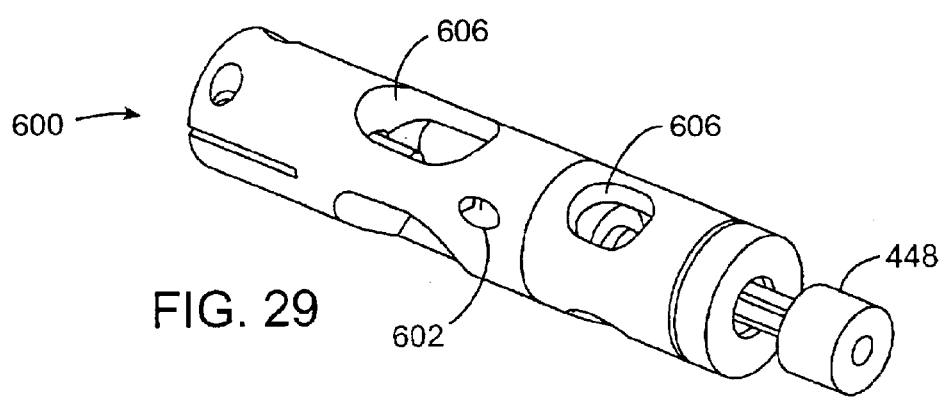
FIG. 29 shows details of the everter fixture.

In the foregoing discussion, an everter fixture 600 is used to position the everter 440 and tool 500 during the eversion process. FIGS. 29–35 show further details of a preferred fixture. As shown in FIGS. 29–30, the fixture 600 can have a cylindrical shape with view ports 606 to allow visual observation of the eversion process. As shown in FIG. 31, the fixture includes a member 610 which receives the everter 440 and a bore 612 receives a forward portion 450 of the handle 448. During the eversion process, the handle 448 is pushed forward to slide the drum assembly 444 along the fingers 442 so as to expand the fingers 442 and open the end of the graft vessel. At the same time, the rear of the everter 440 slides into a bore 452 of the portion 450 until the everter contacts an end wall 454 at which point the drum assembly 444 and the everter 440 move together towards the tool 500 until the graft vessel is everted over the device. Due to a friction fit in the bore 452, the everter 440 is retracted along with the drum assembly 444 when the handle 448 is pulled away from the fixture 600.

The foregoing explanation provides a description of a preferred technique for everting a graft vessel on an implant device. However, the eversion process can be accomplished by other less preferred techniques, some of which are discussed with reference to FIGS. 32–2.

Figure 32:
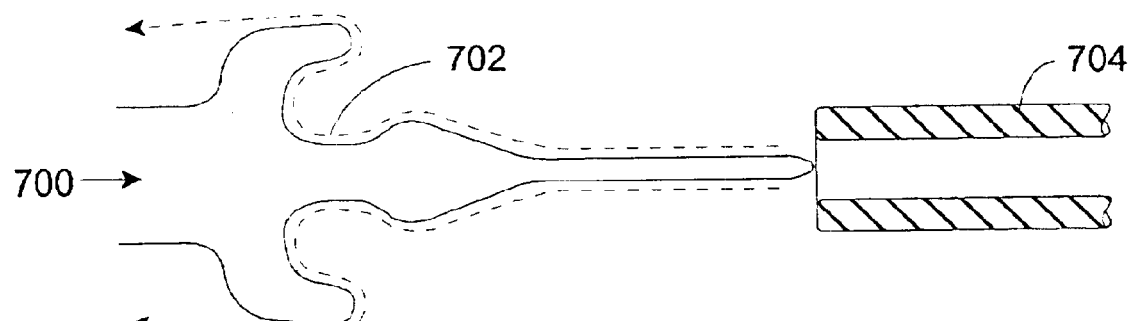
FIG. 32 shows an alternative technique for everting the graft vessel over the anastomosis device.

As shown in FIG. 32, a mandrel 700 could be made in a particular shape such that a vein graft 702 (shown in dotted lines) is pulled and stretched over the shape of the mandrel 700. The mandrel 700 could then be pushed against the implant device 704 such that a proximal portion of the vein graft is inserted into the device and a distal end of the vein graft everted over the outside of the implant device. For instance, the shape of the mandrel can be such that the act of pushing the vein graft off of the mandrel near the implant device will result in the vein being everted over the implant device.

Figure 33A:
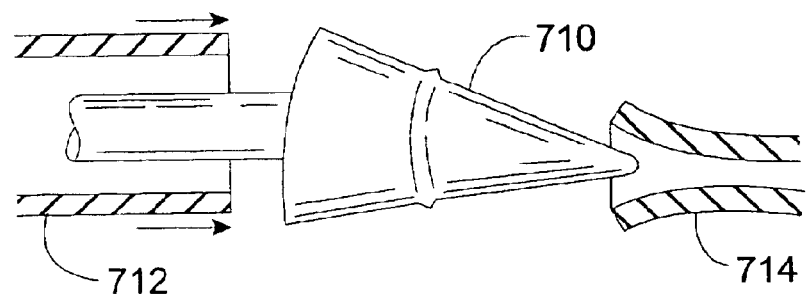
FIGS. 33A and 33B show another alternative technique for everting the graft vessel over the anastomosis device.
Figure 33B:
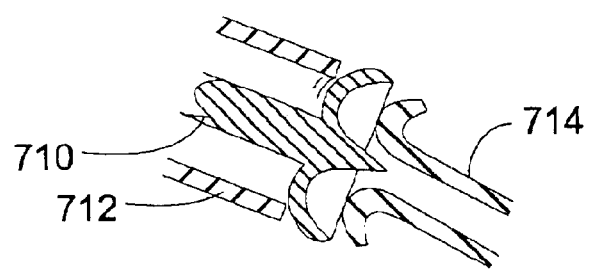

As shown in FIGS. 33A and 33B, a mandrel 710 and collar 712 arrangement can be used to evert a vein graft 714 over an implant device. For instance, an elastomeric cone 710 molded in such a way that it is bistable can be used to achieve eversion of the vein graft bistability means that the mandrel 710 can be deformed from one relaxed state into another relaxed state. In the eversion process, a vein graft 714 could be slid over the tip of the elastomieric cone 710 and the back of the cone could then be actuated by a cylindrical collar 712 to force the cone into its other stable mode which would appear like an inverted umbrella in the process of changing from one configuration to the other configuration, the vein art graft would be everted over the implant device.

Figure 34A:
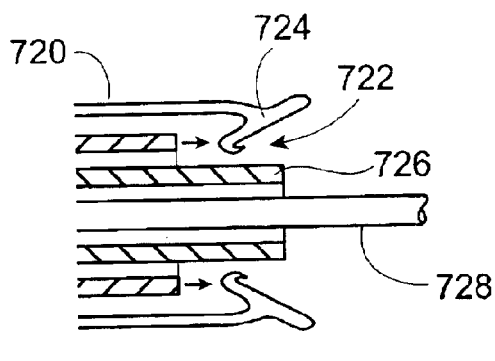
FIGS. 34A and 34B show a further alternative technique for everting the graft vessel over the anastomosis device.
Figure 34B:
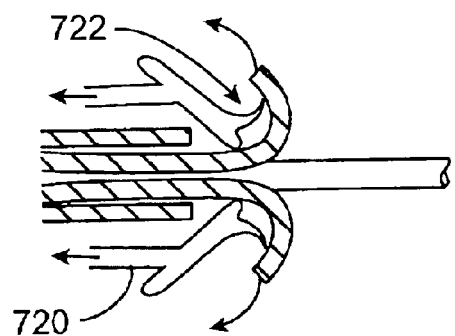

As shown in FIGS. 34A and 34B, a tube 720 could be made with several hooks 722 around the circumference of the inside surface. These hooks 722 could be attached to a hinge joint 724. A vein graft 726 loaded on a mandrel 728 can be could passed through the center of the tube 720 such that the hooks 722 grab onto the graft 726. As the hinged hooks 722 are actuated in an outward fashion, they would evert the vein 726. The tube 720 could then be pulled back, pulling the everted vein 726 over the implant device.

Figure 35:
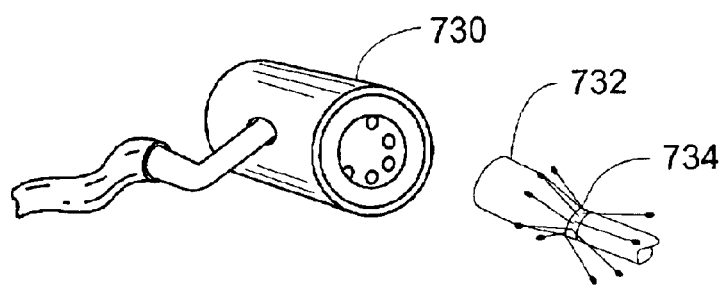
FIG. 35 shows a still further alternative technique for everting the graft vessel over the anastomosis device.

As shown in FIG. 35, a vacuum fixture 730 could be used to grab and hold the vein 732. The vacuum fixture 730 could then be manipulated to evert the vein 732 over the device 734 at which point the vacuum could release the vein graft.

Figure 36:
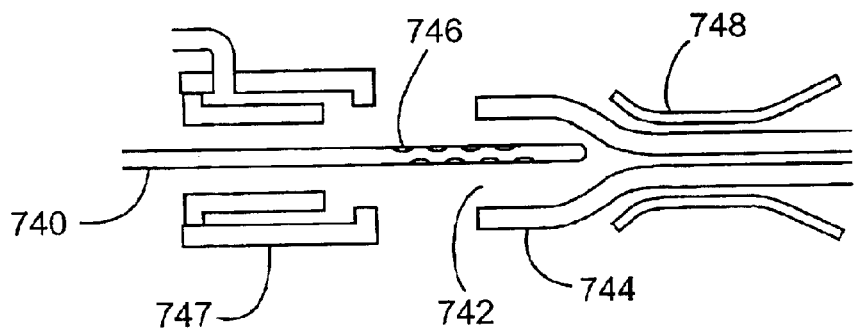
FIG. 36 shows yet another alternative technique for everting the graft vessel over the anastomosis device.

As shown in FIG. 36, a cylindrical mandrel 740 could be inserted into the lumen 742 of the vein graft 744 at which point a vacuum is applied through small venting holes 74,6 in the mandrel 740. The vacuum pressure would affix the vein to the mandrel 740 which is then pulled into a vacuum collar 747. The pressure in the mandrel 740 could then be reversed by blowing gas into the vein graft such that the pressure of the gas from the mandrel 740 (with or without application of vacuum by the collar 747) results in everting the vein around the implant device 748.

Figure 37A:
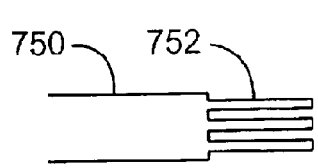
FIGS. 37A and 37B show an additional alternative technique for everting the graft vessel over the anastomosis device.
Figure 37B:
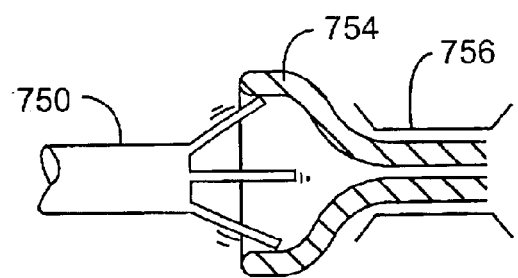

As shown in FIGS. 37A and 37B, an everter 750 having spreading fingers 752 can be used to even the end of the vein graft 754 over the implant device 756.

Figure 38A:
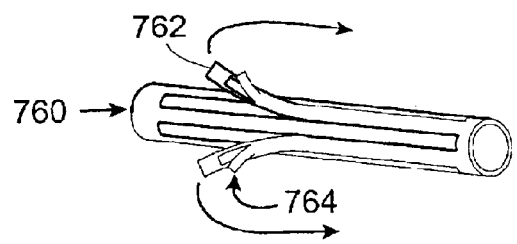
FIGS. 38A and 38B show another alternative technique for everting the graft vessel over the anastomosis device.
Figure 38B:
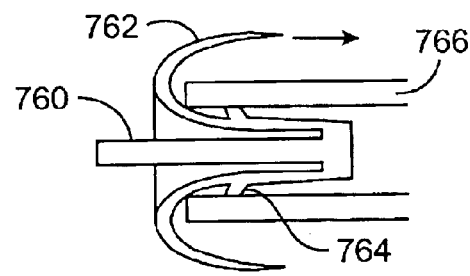

As shown in FIGS. 38A and 38B, a cylindrical tube 760 is made with several pull-tabs 762 around the circumference. Each pull-tab 762 has a corresponding hook 764 which grabs the vein graft 766 as the graft is placed over the tube 760 and onto the hooked tabs 762. As the tabs 762 are peeled back toward the implant device, the vein graft 766 can be everted over the implant device.

Figure 39A:
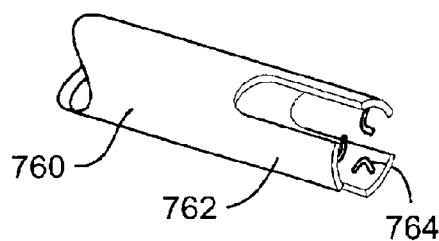
FIGS. 39A and 39B show a further alternative technique for everting the graft vessel over the anastomosis device.
Figure 39B:
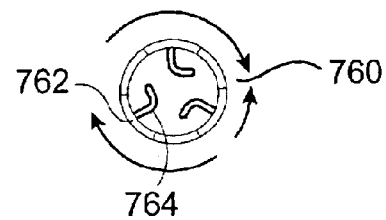

As shown in FIGS. 39A and 39B, a tube 760 could be made with fingers 762 that extend from the end thereof. At the end of each finger 762 is a hook 764 that protrudes toward the inside of the tube 760. This tube 760 could be threaded through the implant device and then collapsed around the vein graft or rotated such as by clockwise rotation such that the hooks 764 grab the outside of the vein graft. The tube 760 could then be drawn through the device and expanded. By pushing the tube 760 back toward the device, the vein graft can be everted over the implant device and by twisting the tube in a direction opposite the direction of the hooks, the vein graft can be released.

Figure 40:
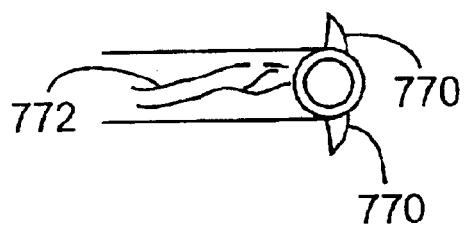
FIG. 40 shows an alternative technique for everting the graft vessel over the anastomosis device.
Figure 41A:
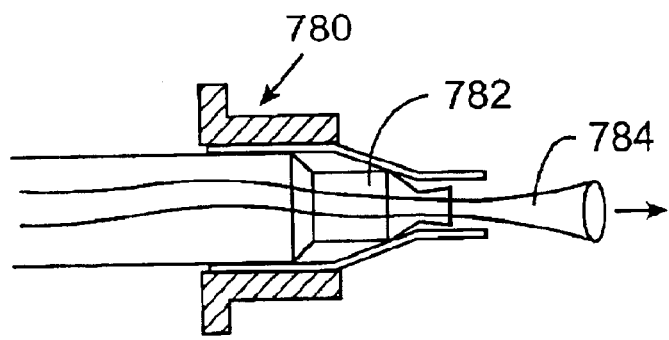
FIGS. 41A–E show another alternative technique for everting the graft vessel over the anastomosis device.
Figure 41B:
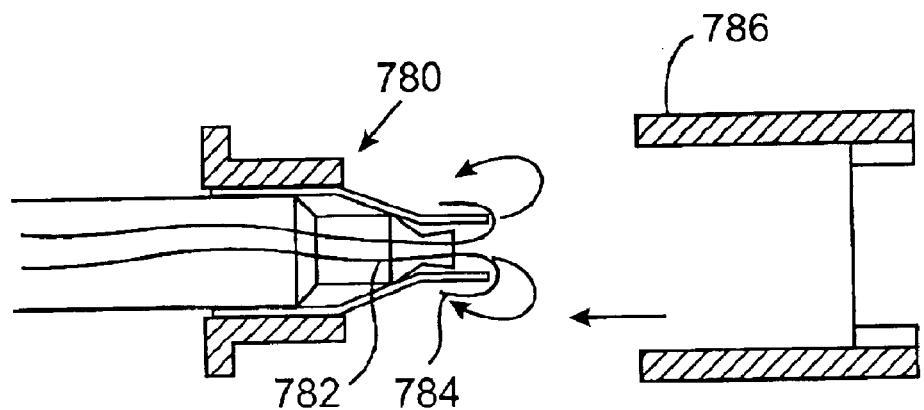
Figure 41C:
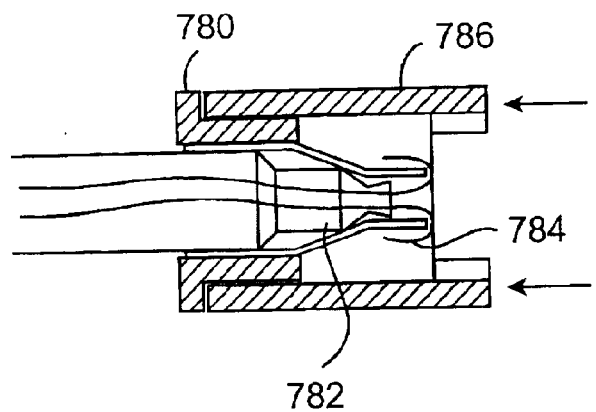
Figure 41D:
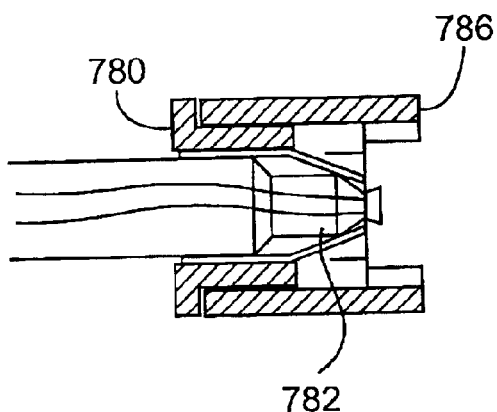
Figure 41E:
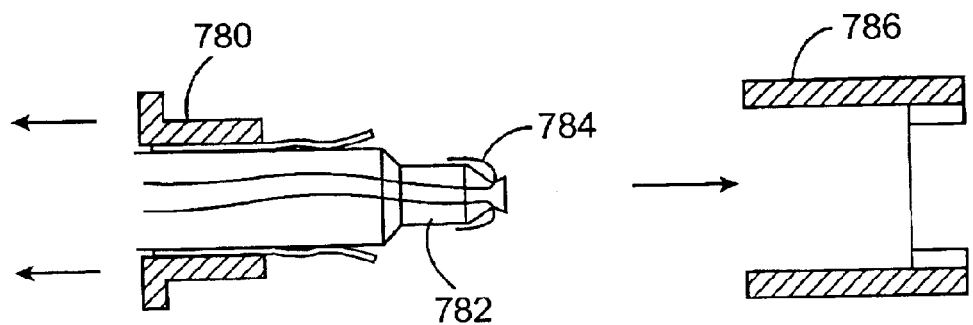

As shown in FIG. 40, a set of jaws or needles 770 on the end of long sutures 772 are threaded through the implant device and tool. The jaws or needles 770 are then affixed to the vein graft 774 at which point the vein graft 774 is drawn through the tool and device. The jaws or needles 770 remain affixed to the vein graft 774 and each individual grabber or needle 770 is pulled in an opposite direction back toward the implant device toward the outside. This peeling back process everts the vein graft 774 over the implant device. The vein graft material where the jaws or needles connect is then cut away leaving only the vein graft everted over the implant device.

As shown in FIGS. 41A–E, a sleeve 780 is placed around the outside of the implant device 782 in order to protect it from damage. The vein graft 784 is pulled through the device and then everted around the protective sleeve 780 using standard forceps. At this point another instrument 786 could approach the implant device and cause the distal tips of the implant device 782 to be penetrated through the vein graft 784. In the same motion, this secondary instrument 786 could push away the protective sleeve 780, leaving only the everted vein graft 784 on the implant device 782. Alternatively, the protective sleeve can be designed to split apart and thus be removed by peeling it off of the implant device.

Figure 42:
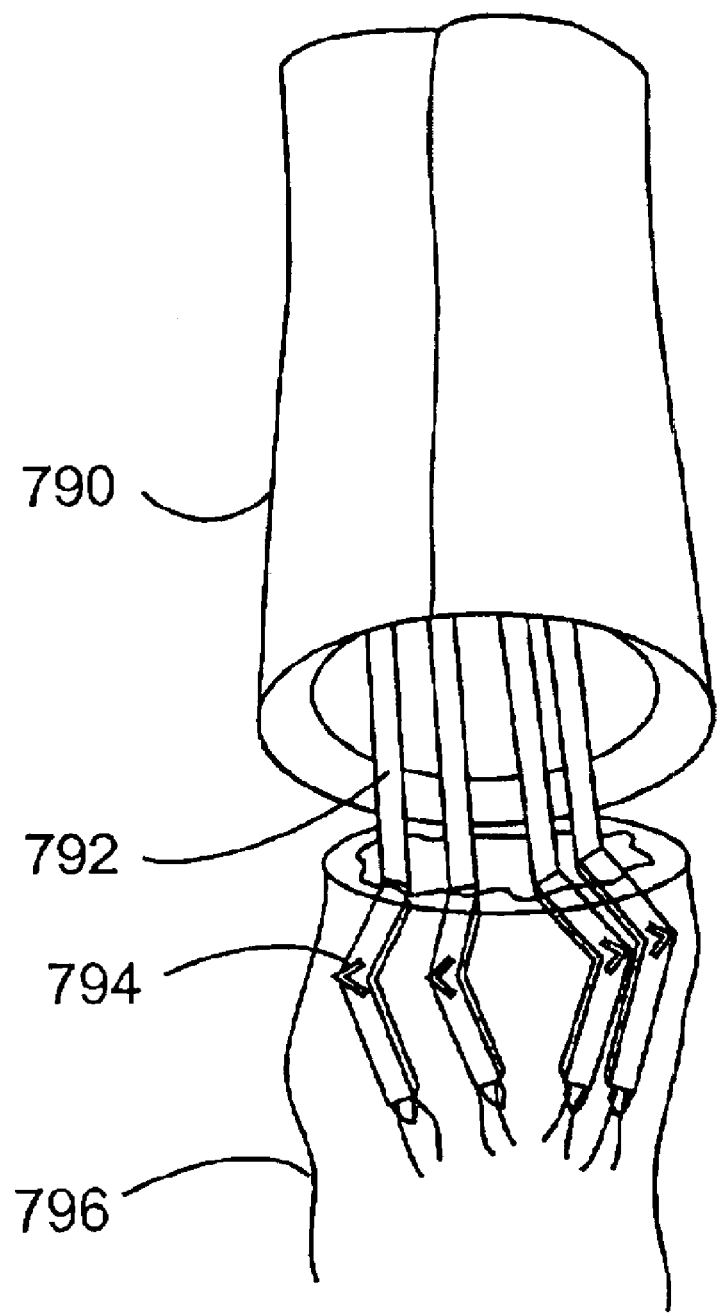
FIG. 42 shows another eversion technique.

As shown in FIG. 42, a tube 790 having a plurality of long fingers 792 extending from the end of the tube 790 can be used to evert the vein graft on each finger 792 is a small hook or barb 794 protruding toward the outside. The fingers 792 are thread through the implant device and tool and the the vein graft 796 is placed over the fingers such that the barbs 794 catch the inside surface of the vein graft 796. The tube 790 and its fingers 792 are then drawn though the tool and implant device. The fingers 792 are then expanded and pushed back around the outside of the implant device. This forward motion of the tube 790 and its fingers 792 release the barbs 794 from the vein graft 796 allowing the tube 790 to be retracted, and the vein graft 796 left everted on the implant device.

Although the invention has been principally discussed with respect to coronary bypass surgery, the anastomosis devices of the present invention may be used in other types of anastomosis procedures. For example, the anastomosis device may be used in femoral-femoral bypass, vascular shunts, subclavian-carotid bypass, organ transplants, and the like.

The anastomosis devices may be made of any known material which can be bent and will retain the bent shape such as stainless steel, nickel titanium alloys, and the like. The hinges or pivot joints which have been discussed above in the various embodiments of the present invention may be designed to concentrate the bending at a desired location.

While the invention has been described in detail with reference to the preferred embodiments thereof, it will be apparent to one skilled in the art that various changes and modifications can be made and equivalents employed, without departing from the present invention.

What is claimed is:

1. A tool configured to evert an end of a graft vessel over an end of an anastomosis device, the tool comprising: an everter configured to engage the end of the graft vessel, said everter expandable both radially and axially from a first configuration to a second configuration to expand the graft vessel for eversion over the end of the anastomosis device.

2. A tool configured to evert an end of a graft vessel over an end of an anastomosis device, the tool comprising: an everter configured to engage the end of the graft vessel, said everter expandable from a substantially conical shape to a substantially cylindrical shape to expand the graft vessel for eversion over the end of the anastomosis device.

3. A system for use in preparing a graft vessel for anastomosis to a target vessel, comprising:
- a deployment tool having a bore therethrough;
- at anastomosis device connected to said deployment tool; and
- a pull-through tool comprising at least one tension element slidable at least partially through said bore and said anastomosis device.

4. The system of claim 3, wherein at least one said tension element is a wire.

5. The system of claim 3, wherein said pull-through tool is substantially flexible.

6. The system of claim 3, wherein the distal end of at least one said tension element is bent.

7. The system of claim 3, wherein said pull-through tool is configured to contact an outer surface of the graft vessel.

8. The system of claim 3, further comprising a protective sleeve adjacent to said anastomosis device.

9. The system of claim 8, wherein said protective sleeve is split table.

10. The system of claim 8, wherein said protective sleeve has a lumen therethrough, said lumen sized substantially the same as the circumference of said anastomosis device.

11. The system of claim 8, wherein said protective sleeve is moveable along said deployment tube.

12. The system of claim 8, wherein said protective sleeve is detachably connected to at least a portion of said anastomosis device.

13. The system of claim 8, further comprising a poke-through tool moveable relative to said protective sleeve.

14. The system of claim 13, wherein said poke-through tool is adapted to urge said protective sleeve in a proximal direction.

15. The system of claim 13, wherein at least a portion of said poke-through tool slides over at least a portion of said protective sleeve.

16. The system of claim 3, further comprising a poke-through tool moveable relative to said protective sleeve.

17. The system of claim 16, wherein said poke-through tool comprises a housing and a membrane connected to said housing.

18. The system of claim 16, wherein said poke-through tool comprises an instrument adapted to cause a portion of said anastomosis device to penetrate said graft vessel.

* * * * *